United States Patent
Veronesi et al.

(10) Patent No.: US 9,284,292 B2
(45) Date of Patent: Mar. 15, 2016

(54) SIALOCHIMERIC COMPOUNDS

(75) Inventors: Paolo Alberto Veronesi, Milan (IT);
Pablo E. A. Rodriguez, Cordova (AR);
Anna Maria Veronesi, Bastia Umbra (IT); Emanuela Peschechera, Milan (IT)

(73) Assignee: THERAPICON S.R.L., Milan (IT)

( * ) Notice: Subject to any disclaimer, the term of this patent is extended or adjusted under 35 U.S.C. 154(b) by 691 days.

(21) Appl. No.: 13/512,306

(22) PCT Filed: Nov. 25, 2010

(86) PCT No.: PCT/EP2010/068229
§ 371 (c)(1),
(2), (4) Date: May 25, 2012

(87) PCT Pub. No.: WO2011/064303
PCT Pub. Date: Jun. 3, 2011

(65) Prior Publication Data
US 2012/0269771 A1  Oct. 25, 2012

(30) Foreign Application Priority Data
Nov. 25, 2009 (IT) .............................. MI2009A2071

(51) Int. Cl.
| | | |
|---|---|---|
| *A61K 31/351* | (2006.01) | |
| *C07D 407/12* | (2006.01) | |
| *C07D 309/14* | (2006.01) | |
| *C07H 19/056* | (2006.01) | |

(52) U.S. Cl.
CPC ............ *C07D 309/14* (2013.01); *C07H 19/056* (2013.01)

(58) Field of Classification Search
CPC ............................ C07H 19/056; C07D 309/14
USPC ................... 424/85.7; 514/459; 549/415, 419
See application file for complete search history.

(56) References Cited

U.S. PATENT DOCUMENTS 8,227,425 B2   7/2012   Veronesi

FOREIGN PATENT DOCUMENTS

WO     WO2008090151 A1    7/2008

OTHER PUBLICATIONS

Almagro-Moreno, Salvador et al., "Insights into the evolution of sialic acid catabolism among bacteria", BMC Evolutionary Biology, 2009: 9:118. p. 9-16.
Aoki, Fy et al. "Influenza virus susceptibility and resistance to oseltarnivir", Antivir Ther. 2007,12 (PT.B. 4, p. 603-16.
Arnberg, Niklas, Ten Feizi, Thilo Stehle "Polyomavirus capsid protein (VP1)", CFG paradigms, 2011.
Babu Y.S. et al. : "Discovery of a novel, highly potent, orally active, and selective influenza neuraminidase inhibitor through structure-based drug design,", J. Med. Chem. 2000, 43 (19): 3482-86.
Bartosch, Birke et al, "Hepatitis B and C Viruses and hepatocellular carcinoma", Viruses, 2010, 2, p. 1504-1509.
Baz M et al., "Characterization of drug-resistant recombinant influenza A/H1N1 viruses selected in vitro with peramivir and zanamivir", Antiviral Res., 2007, 74(2), p. 159-62.
Bernfield M- et al. "Functions of cell surface heparan sulfate proteoglycans." Annu. Rev. Biochem. 1999, 68: p. 729-777 (Abstract).
Bertozzi, Carolyn R., "Research Interests" Bertozzi Group Research (2011) , Unv. of California, Berkeley.
Bolotin S. et al. "Development of a novel real-time reverse-transcriptase PCR method for the detection of H275Y positive influenza A H1N1 isolates." J Virol Methods. Epub 2009 Gen. 30, 2009 Giu.,158 (1-2): p. 190-194. (Abstract).
Brigham, Christopher et al., "Sialic Acid (N-Acetyl Neuraminic Acid) Utilization by Bacteroides fragilis Requires a Novel N-Acetyl Mannosamine Epimerase", Journal of Bacterioiogy, 2009, p. 3629-3638.
Butin-Israeli, Veronika "Simian Virus 40 Infection Triggers a Balanced Network That Includes Apoptotic. Survival, and Stress Pathways", Journal Virology, Apr. 2010, 84 (7), p. 3431-3442.
Campanero-Rhodes, Maria A. et al, "N-Glycolyl GM1 Ganglioside as a Receptor for Simian Virus 40",Journal Virology, Dec. 2007, 81(23), p. 12846-12858.
Carr M.J. et. al, "Rapid molecular detection of the H275Y oseltamivir resistance gene mutation in circulating influenza A (H1N1) viruses." J. Virol. Methods 2008, 153 (2): p. 257-262. (Abstract).
Castle E. et al. "Sequence analysis of the viral core protein and the membrane-associated proteins V1 and NV2 of the flavivirus West Nile virus and of the genome sequence for these proteins.", Virology 1985, 145: p. 227-236. (Abstract).
Centers for Disease Control and Prevention (CDC) "High levels of adamantine resistance among influenza A (H3N2) viruses and interim guidelines for use of antiviral agents—United States. Jun. 2005 influenza season.", MMWR Morb. Mortal Wkly Rep. 2006, 55 (2): p. 44-6 (Abstract).
Centers for Disease Control and Prevention (CDC) "Oseltamivir-resistant 2009 pandemic influenza A (H1N1) virus infection in two summer campers receiving prophylaxis—North Carolina, 2009", MMWR morb. Mortal Wkly Rep. Sep. 11, 2009, 58 (35): p. 969-72. (Abstract).
Chambers T. J. et al, "Flavivirus genome organization, expression, and replication.", Annu. Rev. Microbiol. 1990, 4: p. 649-688 (Abstract).

(Continued)

*Primary Examiner* — Jeffrey S Lundgren
*Assistant Examiner* — Sara E Townsley
(74) *Attorney, Agent, or Firm* — Standley Law Group LLP

(57) ABSTRACT

The present invention discloses a new class of compounds that exhibit an inhibitory effect on influenza virus type A and B, which may or may not be resistant to other drugs, as well as on other types of viruses, such as flavivirus but also on protozoa and other micro-organisms, their preparation methods, pharmaceutical formulations containing them and their use as medicinal products for the treatment of various conditions caused by particular microorganisms, including viruses, bacteria and protozoa, which affect animal and human health.

10 Claims, 5 Drawing Sheets

(56) References Cited

OTHER PUBLICATIONS

Figure 1:
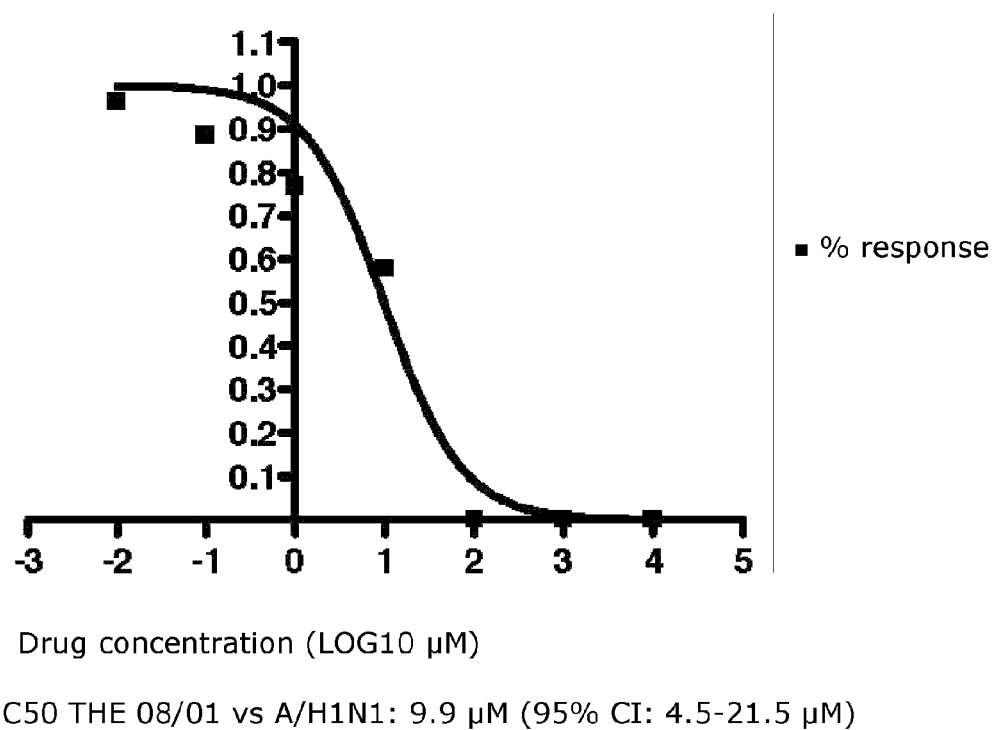

Chen Y. et al. "Dengue virus infectivity depends on envelope protein binding to target cell heparan sulfate.", Nat. Med. 1997, 3: p. 866-71 (Abstract).
Coia G. et al. "Nucleotide and complete amino acid sequences of Kunjin virus: definitive gene order and characteristics of the virus-specified proteins." J. Gen. Virol. 1988, 699: p. 1-21. (Abstract).
Collins P.J. et al. "Structural basis for oseltamivir resistance of influenza viruses", Vaccine Oct. 23, 2009, 27 (45): p. 6317-23, (Abstract).
Colman P. M. et al. "Structure of the catalytic and antigenic sites in influenza virus neuraminidase", Nature 1983, 303: p. 41-44. (Abstract).
D'Ursi P. et al "Virtual screening pipeline and ligand modelling for H5N1 neuraminidase", Biochem. Biophys. Res. Comm. 209 Jun. 12,, 383 (4): p. 445-9 (Abstract).
Das P. et al. "Free energy simulations reveal a double mutant avian H5N1 virus hemagglutinin with altered ceptor binding specificity.", J. Comput. Chem. 2009, 30 (11): p. 1654-63, (Abstract).
Dharan N.J. et al. Oseltamivir-Resistance Working Group "Infections with oseltamivir-resistant influenza A(H1N1) virus in the United States." JAMA Epub Mar. 2, 2009, Mar. 11, 2009, 301 (10), p. 1034-41. (Abstract).
Doms R.W. et al. "Variant influenza virus hemagglutinin that induces fusion at elevated pH", J. Virol. 1986, 57 (2): p. 603-613 (Abstract).
Dreux, Marle ne et al, "Receptor Complementation and Mutagenesis Reveal SR-BI as an Essential HCV Entry Factor and Functionally Imply Its Intra- and Extra-Cellular Domains", PLOS Pathogens, Feb. 2009, 5 (2), p. 1-17.
Ewers, Helge et al. "GM1 structure determines SV40-induced membrane invagination and infection", ABST—Nature Cell Biology, 2010, 12, p. 11-18.
Fumari, Kshama et al, "Receptor binding specificity of recent human H3N2 influenza viruses", Virology Journal, 2007, 4 (42). p. 1-12.
Gautam, Mondal et al, "Alterations of glycan branching and differential expression of sialic acid on alpha fetoprotein among hepatitis patients", Glycoconjugate Journal, 28 (1), 2001 p. 1-9.
Gooskens J. et al, "Morbidity and mortality associated with nosocomial transmission of oseltamivir-resistant influenza A (H1N1) virus." JAMA Epub Mar. 2, 2009, Mar. 11, 2009, 301 (10): p. 1042-6. (Abstract).
Kopecky J. et al. "A putative host cell receptor for tick-borne encephalitis virus identified by anti-idiotypic antibodies and virus affinoblotting.", Intervirology 1999, 42: 9-16 (Abstract).
Govorkova, Elena A. et al., "Competitive Fitness of Oseltamivir-Sensitive and -Resistant Highly Pathogenic H5N1 Influenza Viruses in a Ferret Model", J.Virol., 2010, 84, 16, p. 8042-8050.
Guglielmi, Kristen M. et al., "Reovirus Binding Determinants in Junctional Adhesion Molecule-A", J. Biol. Chem. 2007, 282 (24), p. 17930-40.
Gulati, Shelly et al. "Deletions of neuraminidase and resistance to oseltamivir may be a consequence of restricted receptor specificity in recent H3N2 influenza viruses", Virology Journal 2009, 6,22, p. 1-15.
Guo L. et al. "Rapid identification of oseltamivir-resistant influenza A(H1N1) viruses with H274Y mutation by RT-PCR/ restriction fragment length polymorphism assay." Antiviral Res, Epub 2009 Gen. 31, Apr. 2009, 82 (1): p. 29-33 (Abstract).
Hahn C.S. et al. "Comparison of the virulent Asibi strain of yellow fever virus with the 17D vaccine strain derived from it", Proc. Natl Acad. Sci. USA. 1984, 84: p. 2019-2023 (Abstract).
Hahn Y.S. et al "Nucleotide sequence of dengue 2 RNA and comparison of the encoded proteins with those of other flaviviruses,", Virology 1988, 162: p. 167-180.
Hall, Kathryn et al., "Unity and Diversity in the human adenoviruses: exploiting alternative entry pathways for gene therapy", Biochem. J., 2010. 431, p. 321-336.
Herrier G. et al. "9-O-acetylated sialic acid, a receptor determinant for influenza C virus and coronavirus" Behring Inst. Mitt. 1991, 89: p. 177-84 (Abstract).

Herrier Georg, et al., "A synthetic sialic acid analogue is recognized by influenza C virus as a receptor but is resistant to the receptor-destroying enzyme", J. Biol. Chem. 1992, 2567 (8): p. 12501-12505 (Abstract).
Hurt AC et al., "Oseltamivir resistance and the H274Y neuraminidase mutation in seasonal, pandemic and highly pathogenic influenza viruses", Drugs. 2009, 69, 18. p. 2523-31.
Hurt AC, et al., "Emergence and spread of oseltamivir-resistant A(H1N1. influenza viruses in Oceania, South East Asia and South Africa", Antiviral Res., 2009,83,1,p. 90-3.
Ilyushin, Natalia A. et al., "Effect of Neuraminidase Inhibitor—Resistant Mutations on Pathogenicity of Clade 2.2 A/Turkey/15/06 (H5N1) Influenza Virus in Ferrets", PLOS Pathogens, 2010, 6, 5, p. 1-11.
Itzstein L.M. von el al. "Rational design of potent sialidase-based inhibitors of influenza virus replication", Nature 1993, 363 (6428): p. 418-423 (Abstract).
Iwata T. el al. "Theoretical analysis of binding specificity of influenza viral hemagglutinin to avian and human receptors based on the fragment molecular orbital method.", Comput. Biol. Chem. 2008, 32 (3):p. 198-211 (Abstract).
Jackson T. et al. "Arginine-glycine-aspartic acid-specific binding by foot-and-mouth disease viruses to the purified integrin alpha(v)beta3 in vitro", J. Virol. 1997, 71: p. 8357-836-1 (Abstract).
Jeong, Hee Gon et al., "The Capability of Catabolic Utilization of N-Acetylneuraminic Acid, a Sialic Acid, Is Essential for Vibrio vulnificus Pathogenesis", Infection and Immunity, 2009, p. 3209-3217.
Johansson SM et al, "Multivalent sialic acid conjugates inhibit adenovirus type 37 from binding to and infecting human corneal epithelial cells", Antiviral Research, Feb. 2007, 73 (2), p. 92-100.
Kimura, T. et al. "Analysis of virus-cell binding characteristics on the determination of Japanese encephalitis virus susceptibility." Arch. Virol. 1994, 139, p. 239-251. (Abstract).
Kirchner, Eva et al., "Structure of Reovirus delta 1 in Complex with its Receptor Junctional Adhesion Molecule-A", PLOS Pathog., 2008, 4 (12), p. 1-12.
Wang C.C. et al. "Glycans on influenza hemagglutinin effect receptor binding and immune response.", Proc. Natl. Acad. Sci. U.S.A., Oct. 12, 2009, (Abstract).
Wilson I. A. et al. "Structure of the heamoagglutinin membrane glycoprotein of influenza virus at 3 Å resolution", Nature 1981, 289: p. 366-73, (Abstract).
Xu D. el al. "Distinct glycan topology for avian and human sialopentasaccharide receptor analogues upon binding different hemoagglutinings: a molecular dynamics perspective.", J. Mol. Biol. Epub. 2009 Feb. 5, 2009, 387 (2): p. 465-91 (Abstract).
Yamashita M. et al., "CS-8958, a prodrug of the new neuraminidase Inhibitor R-125489, shows long-acting anti-influenza virus activity", Antimicrob. Agents Chemother. 2009, 53(1): p, 186-92 (Abstract).
Yen, Hui-Ling et al., "Neuraminidase Inhibitor-Resistant Recombinant A/Vietnam/1203/04 (H5N1) Influenza Viruses Retain Their Replication Efficiency and Pathogenicity In Vitro and In Vivo", J. Virol., 2007, 81, 22, p. 12418-12426.
Lavillette, Dimitri et al., "Hepatitis C Virus Glycoproteins Mediate Low pH-dependent Membrane Fusion with Liposomes", J. Biol. Chem. 2006 281, 7, pp. 3909-3917.
Lehman, F. "The evolutionary history of sialylation. Perspective from fish genomes", 2004.
Lewis, Amanda et al., "Innovations in host and microbial sialic acid biosynthesis revealed by phylogenomic prediction of nonulosonic acid structure", Pnas, 2009, 106 (32), p. 13552-13557.
Lin, Jr-Shiuan et al., "Distinct roles of complement receptor 3, Dectin-1, and sialic acids in murine macrophage interaction with Histoplasma yeast", Journal of leukocyte Biology-JLB, Jul. 2010, 88, p. 1-12.
Lindenbach, Brett D. et al, "Complete Replication of Hepatitis C Virus in Cell Culture", Science, Jul. 2005 309, p. 623-626.
Lobigs M. et al. "Host cell selection of Murray Valley encephalitis virus variants altered at an RGD sequence in the envelope protein and in mouse virulence.", Virology 1990. 176: p. 587-595 (Abstract).

(56) References Cited

OTHER PUBLICATIONS

Mackow E. et al. "The nucleotide sequence of dengue type 4 virus: analysis of genes coding for nonstructural proteins.", Virology 1987, 159: p. 217-228. (Abstract).

Maganti, Srivinas et al., "The role of sialic acid in Opsonin-dependent and Opsonin-Independent Adhesion of Listeria monocytogenes to Murine Peritoneal Macrophages", Infection and Immunity, Feb. 1998, p. 620-626.

Maldov D.G. et al. "Tick-borne encephalitis virus interaction with the target cells," Arch. Virol. 1992, 127: p. 321-325, (Abstract).

Wadstrom, Torkel et al., "Glycosaminoglycan and sialic acid binding microbial proteins in gut tissue adhesion and invasion" OH University, Lund, Sweden, 1998, p. 45-60.

Mandl C.W. et al. "Sequence of the structural proteins of tick-borne encephalitis virus (western subtype) and comparative analysis with other flaviviruses.", Virology 1988, 166: p. 197-205. (Abstract).

Martindale 33 rd Ed. (2002), p. 639-43.

Mason P.W. et al. "Sequence of the dengue-1 virus genome in the region encoding the three structural proteins and the major nonstructural protein NS1.". Virology 1987, 161: p. 262-267 (Abstract).

McAda P.C. et al. "Partial nucleotide sequence of the Japanese encephalitis virus genome.", Virology 1987, 158: p. 348-360 (Abstract).

Monath T.P. et al. "Flaviviruses.", in Fields B.N., Knipe D.M., Howley P. M., Editors. Fields Virology, 3rd ed., vol. 1, 1996, Philadelphia, Pa, Lippincott-Raven Publishers, p. 961-1034 (Abstract).

Moscona A. "Medical management of influenza infection". Annu. Rev. Med. 2008, 59: p. 397-413 (Abstract).

Neff S. et al. "Foot-and-mouth disease virus virulent for cattle utilizes the integrin alpha(v)beta3 as its receptor," J. Virol., 72: p. 3587-3594 (Abstract).

Neu, Ursula et al. "Structural basis of GM1 Ganglioside recognition b simian virus 40", PNAS, Apr. 2008, 105 (13, p. 5219-5224.

Nilsson, Emma C. et al. "Sialic Acid is a Cellular Receptor for Coxsachievirus A24 Variant ,an Emerging Virus with Pandemic Potential", Journal of Virology; May 2008, 82 (6), p. 3061-3068.

Nizet, Victor and Jeffrey D. Esko "Bacterial and Viral Infections", Essentials of Glycobiology, 2009.

Okomo-Adhiambo M et al., "Host cell selection of influenza neuraminidase variants: implications for drug resistance monitoring in A(H1N1) viruses", Antiviral Res. 2010, 85, 2, p. 381-8.

Prota, Andrea E. et al, "Crystal structure of human junctional adhesion molecule 1: Implications for reovirus binding", PNAS, Apr. 2003, 100 (9), p. 2-6.

Qian, Mengding and Billy Tsai, "Lipids and Proteins Act in Opposing manners to regulate Polyomavirus Infection", Journal of Virology. 2010. 84(19) p. 9840-9852.

Ramos-Castaneda J. et al. "A 65-kDa trypsin-sensible membrane cell protein as a possible receptor for dengue virus in cultured neuroblastoma cells." J. Neurovirol. 1997, 3: p. 435-440 (Abstract).

Rey F.A. et al. , "The envelope glycoprotein from tick-borne encephalitis virus at 2 angstrom resolution.". Nature 1995, 375: p. 291-298. (Abstract).

Rice C.M. et al. "Nucleotide sequence of yellow fever virus: implications for flavivirus gene expression and evolution." Science 1985, 229: p. 726-733. (Abstract).

Roivainen M. et al. "Entry of coxsackievirus A9 into host cells: specific interactions with alpha v beta 3 integrin, the vitronectin receptor." Virology 1994, 203: p. 357-365 (Abstract).

Ruoslahti E. et al. "New perspectives in cell adhesion: RGD and integrins.", Science 1987, 238: p. 491-497 (Abstract).

Salas-Benito J.S.: del Angel R.M. "Identification of two surface proteins from C6/36 cells that bind dengue type 4 virus," J. Virol. 1997, 71: p. 7246-7252 (Abstract).

Schmidt, Peter M. et al., "A Generic System for the Expression and Purification of Soluble and Stable Influenza Neuraminidase", Plos one, 2011, 6, 2, p. 1-13.

Schoenhofen, Ian C. et al., "Elucidation of the CMP-pseudaminic acid pathway in Helicobacter pylori: synthesis from UDP-N-acetylglucosamine by a single enzymatic reaction", Glycobiology, 2006, 16 (9). p. 8C-14C.

Zhang, Wei et al, "Crystal structure of the swine-origin A (H1N1)-2009 influenza A virus hemagglutinin (HA) reveals similar antigenicity to that of the 1918 pandemic virus", Protein Cel, 2010, 1(5), p. 457-647.

Schwegmann-Wessels C. et al. "Sialic acids as receptors determinants for coronavirus" Glycoconj. J. 2006, 23 (1-2): p. 51-8.

Severi, Emmanuele et al., "Sialic acid transport in Haemophilus influenzae is essential for lipopolysaccharide sialytation and serum resistance and is dependent on a novel tripartite ATP-independent periplasmic transporter", Molecular Microbiology, 2005 58(4), p. 1173-1185.

Severi, Emmanuele et al., "Sialic acid utilization by bacterial pathogens" Microbiology, 2007, 153, p. 2817-2822.

Shriver Z. et al—Context-specific target definition in influenza virus hemagglutinin-glycan receptor interactions.—Chem Biol. Aug. 28, 2009, 16(8), p. 803-814.

Spadafora, Carmenza et al. "Complement receptor 1 is a sialic acid-Independent Erythrocyte Receptor of Plasmodium falciparum", Plos, 2010, 6(6), p. 1-13.

Sreevatsan, Srinand et al., "Restricted structural gene polymorphism in the Mycobacterium tuberculosis complex indicates evolutionarily recent global dissemination", Proc. Natl. Acad. Sci, 1997, 94, p. 9864-9874.

Stehle, Thilo and Stephen C. Harrison. "High-resolution structure of a polyomavirus VP1—oligosaccriaride complex: implications for assembly and receptor binding", EMBO journal, 1997, 16 (16). p. 5139-5148.

Stephenson I. et al.—"Neuraminidase Inhibitor Resistance adfter Oseltamivir Treatment of Acute Influenza A and B in Children"—Clin. Infect. Dis. Feb. 15, 2009 48(4), p. 389-96.

Stephenson I., et al. "Antiviral treatment and prevention of seasonal influenza: a comparative review of recommendations in the European Union", J. Clin. Virol. 2008. 42 (3), p. 244-8 (Abstract).

Takahashi T. el al. "Duck and animal pandemia influenza A viruses retain sialidase activity under low pH conditions" J. Biochem. 2001, 130: p. 279-283 (Abstract).

Takashi Angata and Ajit Varki "Diversity in the Sialic Acids and Related alpha-Keto Acids: A Revolutionary Perspective", Chem. Rev., 2002, 102. p. 446-449.

Taylor N.R., von Itzstein M. "Molecular modeling studies on ligand binding to sialidase from influenza virus and the mechanisms of catalysis.", J. Med. Chem. 1994, 37(5): p. 616-24 (Abstract).

Todar, Kenneth "Mechanisms of Bacterial Pathogenicity", Todar's Online Texbook of Bacteriology, 2011.

Trent D.W. et. al. "Partial nucleotide sequence of St. Louis encephalitis virus RNA: structural proteins, NS1, ns2a, and ns2b.", Virology 1987, 156: p. 293-304. (Abstract).

Tyler K.L. et al "Pathogenesis of viral infection." Fields Virology. 3rd ed., Fields B.N., Knipe D.M. Howley P.M. Editors. Philadelphia 1996, Pa. Lippincott-Raven, p. 173-218 (Abstract).

Varghese J. N. et al. "Structure of the influenza virus glycoprotein antigen neuraminidase at 2.9 Å resolution", Nature 1983, 303: p. 35-40 (Abstract).

Vimr, Eric R. et al., "Diversity of Microbial Sialic Acid Metabolism", Microb. Molec. Rev., 2004, p. 132-153.

Zurcher, Thomas et al., "Mutations conferring zanamivir resistance in human influenza virus N2 neuraminidases compromise virus fitness and are not stably maintained in vitro", Journal of Antimicrobial Chemotherapy, 2006, 58, p. 723-732.

Drug concentration (LOG10 µM)

EC50 THE 08/01 vs A/H3N2: 15.4 µM (95% CI: 2.5-95.8 µM)

Drug concentration (LOG10 μM)

EC50 THE 08/01 vs B: 125.5 μM (95% CI: 7.8-2014.0 μM)

Figure 4 – THE 08/01 vs Flu A/H1N1(H275Y) + Flu A/H1N1

THE 08/01

- A/H1N1(H275Y)
- A/H1N1

(Fractional response vs Drug Concentration (LOG10 uM))

- EC50 THE 08/01 vs A/H1N1(H275Y): 14.5 µM (95%CI: 5.2-41.5 µM);
- EC50 THE 08/01 vs A/H1N1: 16 µM (95%CI: 3.1-81.8 µM).

FIGURE 5
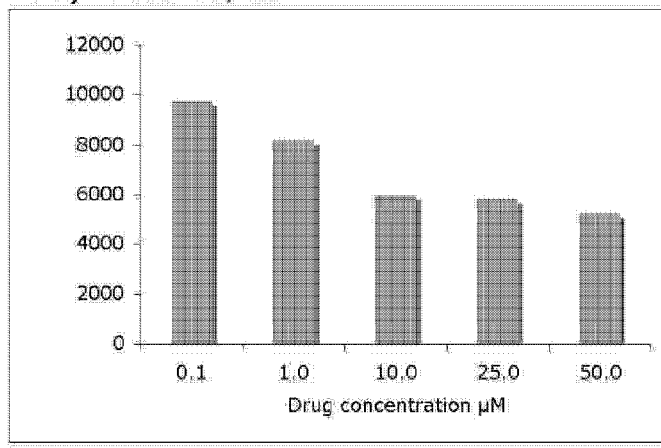
A) THE 08/01
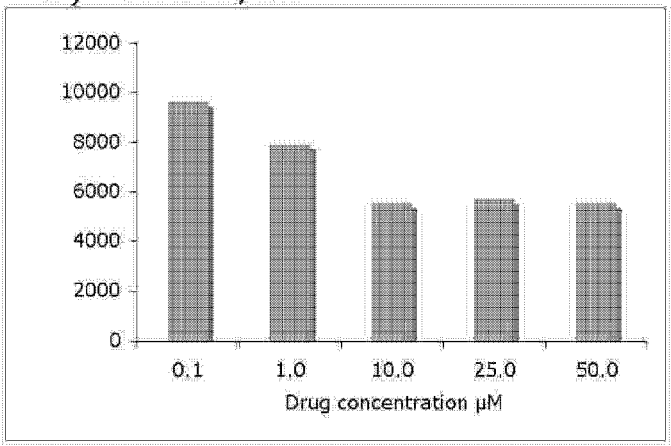
B) THE 10/01
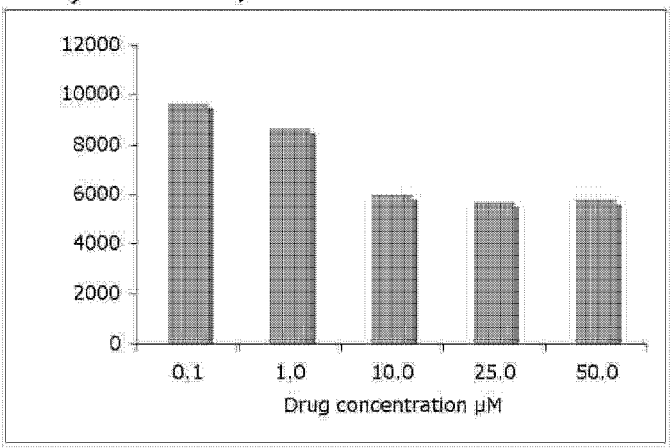
C) THE 10/09

SIALOCHIMERIC COMPOUNDS

The present invention is generally concerned with a new class of compounds characterized by exhibiting an inhibitory effect on influenza virus type A and B, which may or may not be resistant to other drugs, as well as on other types of viruses, such as flavivirus but also on protozoa and other micro-organisms, their preparation methods, pharmaceutical formulations and their use as medicinal products for the treatment of various conditions caused by particular microorganisms, including viruses, bacteria and protozoa, which affect animal and human health.

DESCRIPTION

The invention relates generally to a new class of compounds characterized in that they exhibit an inhibitory effect on any of influenza virus type A and B, which may or not be resistant to other drugs, on other types of micro-organisms, including viruses such as flavivirus and protozoa amongst others, their preparation methods, pharmaceutical formulations containing them and their use as medicinal products for the treatment of various conditions affecting human or animal health resulting from infections with said microorganisms such as viruses, bacteria and protozoa.

Although the influenza virus types A and B are among the most well known viruses by virtue of being the main cause of influenza pandemics, other types of viruses such as flavivirus, particularly HCV, and retroviruses, particularly HIV, and protozoa, particularly malaria plasmodium and tripanosomiasis, can develop into much more serious pathological conditions and cause millions of deaths worldwide each year.

These introductory remarks are thus related to the specificity demonstrated by the viral enzymes hemagglutinin (HA) and neuraminidase (NA) to bind the sialic acid (known also as N-acetyl-neuraminic or more simply neuraminic acid, also identified by the acronyms NANA or Neu5Ac, here characterized by the acronym SA) which is exposed by the sialilated glycans on the surface of the host cell, and which allow the virus to enter or to exit by complicated cyclic and multifactorial mechanisms depending by factors unknown until now (1)(2)(3). Consequently, as from 1974 there has been a continuous search to identify active drugs able to inhibit those enzymes, and the viral replication as well, has been developed, thus already observing a peculiar efficacy of some analogs of sialic acid, which is then hereby represented for convenience.

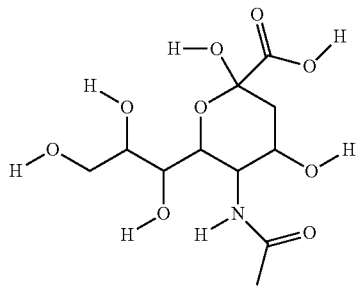 [SMILES: CC(=O)NC1C(O)CC(O)(C(=O)O)OC1C(O)C(O)CO]

Furthermore, protozoa and other microorganisms generally use a similar mechanism mediated from the typical adhesion of HA or NA enzymes of these monocellular pathogens to the sialic acid exposed by the sialilated glycans on the surface of the target cell. The results obtained during the last decade with some antiviral drugs, particularly SA analogs, have been undermined by the development of unexpected resistances, due to the surprising capacity of viruses and of micro-organisms to rapidly evolve by modifying their vital and reproductive mechanisms, so that the efficacy of those drugs is reduced or ineffective as a result of the micro-organisms varying degrees of resistance.

Viral pharmaco-resistance development against both adamantane derivatives (M2 protein inhibitors) and oseltamivir has recently been reported. Some virus strains show an increasing resistance every day against adamantine derivatives in up to about 40% of cases, while oseltamivir resistance has been reported in about 15-20% of all A/H1N1 viruses cases. In fact the most typical characteristic of viral envelope is the presence of radial projections, which in the specific case of influenza viruses type A and B, is corresponding to HA (4)(5)(6) and to NA (7)(8)(9)(10).

In the viral envelope of the type A strain there is also present the homotetrameric M2 protein, which has an important role for the viral depletion.

Furthermore, the influenza virus type C presents a glycoprotein known as hemoglutinin-esterase fusion (HEF) which is responsible for three biological activities: receptor binding (H), receptor inactivation (E) and fusion (F) (11)(12)(13). The antiviral products of first generation (mostly adamantine derivatives such as amantadine, rimantadine, memantine and other similar compounds) block the M2 protein of the ionic channel of influenza virus type A.

The blockade of the entrance flow of $H^+$ ions through $M_2$ protonic channel inhibits the viral depletion and inhibits the release into the cytoplasm of free ribonucleoproteins. The above happens only for influenza virus strain A, and not for strain B, where $M_2$ protein is absent.

For about ten years antiviral strategy has been directed to developing second generation antiviral drugs capable of selectively inhibiting the neuraminidase (NA) of the envelope of influenza virus type A and B. The NA enzyme promotes the viral depletion and the release of the newly produced viruses into the infected cells. It is likely that neuraminidase inhibitors block the active site of neuraminidase so that they do not engage the residues of sialic acid present on the surface of host cells and of viral envelopes.

In fact, since 1999 a second class of selective neuraminidase inhibitors such as zanamivir and oseltamivir has been introduced into clinics. The first one can be administered only by inhalation route being scarcely absorbed by oral the route (about 2%) and therefore it is indicated only for influenza prophylaxis. Only oseltamivir shows systemic effects following oral administration, but nowadays, as previously observed, shows a high incidence of viral resistance. Another new inhibitor of NA, identified in the literature as CS 89958 (active metabolite of compound identified as R-125489)(14), which is at final stage of clinical experimentation, has the advantage of a long activity, being inactivated with difficulty by enzymes, but presents, like zanamivir, the limitation that it is administrable topically only by nasal inhalation, so that may used only for prevention.

Moreover, there is an increasing alarm among scientists, because many international publications report increasing numbers of viral mutations and fusions, more particularly of virus type A, which yield resistant variants are very pathogenic and unpredictably aggressiveness. In this connection it is worth noting that in recent years the avarian influenza virus type A (H5N1) and swine influenza type A (H1N1) have been regarded by scientists as a serious risk because they could generate very dangerous pandemics caused by oseltamivir-resistant virus strains, oseltamivir being the only available product suitable for oral route administration.

In deed, as far the pharmacoresistance is concerned, as already observed, an increasing incidence of viral strains resistant to adamantane derivatives (15)(16)(17)(18)(19) has been reported. The most serious finding is that the resistance seems to be consequent to the chronic and large use of memantine in Alzheimers and of amantadine in Parkinson disease, at doses much lower than those to inhibit the antiviral activity, thus leading to the selection of resistant strains of influenza virus type A.

Moreover, more recent publications have stressed the presence of virus type A strains, isolated from seasonal epidemic diseases (swine influenza, type A/H1N1), showing genetic mutations with resistance to oseltamivir, the sole neuraminidase inhibitor which can be administered by oral route (20)(21)(22)(23)(24)(25), with the result that it is extremely difficult to save those patients infected by those oseltamivir-resistant strains.

By taking into account the infecting steps how enzymes of referred pathogens are utilised, it is known that HA is responsible for the first phase wherein the virus or the micro-organism (bacterium or protozoa or other) binds to the cellular wall of the host cell. In fact, HA binds the unengaged residues of sialic acid of the glycoconjugates of cells wall, whose expression is pH-dependent.

Therefore, an HA inhibitor could prevent the adhesion (viral, bacterial or protozoal), to the surface of host cell, so that it could lead, in the specific case of influential virus type A and B, to a substantial reduction of the number of virus, which enters, completes the reproductive cycle, and is released, so extending the infection to other cells. No suitable HA inhibitor has been yet found and consequently no HA inhibitor is available on the market. In view of the above, it is likely that until now there is no way to contrast the above initial phase wherein HA binds the sialylated glycans exposed on the surface of the host cell membrane. The literature describes however a low affinity of HA for SA, but omits to report that some authors have already described that pH variations may interfere with the fusion mechanism of various strains of influenza virus (26)(27).

Finally as of yet no products have been reported which are capable of inhibiting the glycoproteins and proteins responsible of at least two of the described phases and which may thus be capable of inhibiting, either sequentially or simultaneously, the HA and/or the M2 protein and/or neuraminidase (NA), or which can interfere, either sequentially and/or simultaneously, on at least two or three mechanisms involved in the viral replication, factors that could remarkably increase the potency of the drug, while also minimizing the onset of resistance.

Moreover, other infections sustained by flaviviruses, such as hepatitis type C, yellow fever and Dengue fever, are very common in the parts of the world and produce high pathogenicity and mortality levels, so that they are still causing an increasing number of infected patients and of deaths. For these pathologies, there are no drugs available which are able to ensure an effective treatment. However, the current strategy against the hepatitis type C virus (HCV) is to inhibit with ribavirin (as monophosphate) the synthesis of guanosine monophosphate, thus reducing the intracellular levels. In recent clinical protocols ribavirin has been associated to pegylated interferon alfa-2a or pegylated interferon alfa-2b, which have been available on the market for some years, but with uncertain results.

In addition, there are no available medicinal substances capable of adequately treating initial or acute phases of viral infections sustained by other flavivirus leading a high number of deaths. Today it is only possible to establish a prophylaxis with vaccines, but, in view of the scarcity of the available doses, only allow to limit the epidemic outbreak, as it happens for yellow fever. The lack of specific drugs to treat the diseases caused by flavivirus makes the above infections extremely dangerous, because they cause a high incidence of mortal events.

On the basis of the above, there is an urgent and pressing need for new antiviral compounds where an individual molecule is capable of inhibiting with a multiple and combined, consecutive and simultaneous mechanism the viral replication in order to provide a broad spectrum of activity against a series of other virusal pathogens for men and mammals, but which also prevent the pharmacoresitance of influenza virus type A and type B and of the several variants which are expected during the next few years.

In view of the fact that the mechanism used by the viruses to bind to the wall of the host cell in order to internalize and internally multiply is very similar to those used by other pathogens of humans and mammals, compounds presenting a multiple effect could be useful also for these infections. In fact, bacteria, plasmodia and other monocellular infecting agents at the initial stage of infection of the host cell bind the SA of glycoproteins on the cell surface, by using similar enzymes to HA and NA. Therefore, also bacterial and viral and mixed bacterial-viral infections and also other pathogenic microorganisms, with a high mortality in the worldwide population, can be inhibited by the same compounds for which there is an increasing necessity.

Rationale of Current Antivirals and of Those of the Invention

Colman P. M. et al. in WO 92/06691 (PCT/AU90/00501 published on 30 Ap. 1992), Itzstein L. M. von et al. in the patent EP 0539204 A1 (European patent application n. 92309684.6 published on 28 Apr. 1993), and also the same Itzstein L. M. von e al. in the patent WO91/16320 (application PCT/AU91/00161 published on 31 Oct. 1991) describe compounds binding the viral NA, being consequently considered as in vitro inhibitors of viral activity. Similarly, in 1993 von Itzstein describes in the well known publication "Nature" (28) the rational effect of sialidase inhibitors on the reproduction cycle of influenza virus. Bischofberger N. W. et al. in U.S. Pat. No. 5,952,375 (application U.S. Ser. No. 08/606,624 filed on 26 Feb. 1996) shows new NA inhibiting compounds. The authors Babu Y. S. et al. (29) and the International Publication WO99/33781 (international application PCT/US98/26871, published on 8 Jul. 1999) show a series of other compounds defined as specific NA inhibitors. All most recent antivirals, inhibiting NA such as zanamivir, oseltamivir, peramivir, laninamivir are analogs of sialic acid (SA) and therefore they are competing only with the mechanism of inhibition of the viral NA of some influenza strains type A, but they are not and cannot be used either to treat influenza virus type B nor other viral diseases. Consequently, it does not appear also that their use could be extended also to other monocellular microorganisms.

Similarly, it is a current medical practice, as described in the well known publication Martindale 33.th Ed. (2002) pages 639-43 (30), to combine in human subjects affected from other viral pathologies the simultaneous administration of analogs of purinic nucleosides, such as ribavirin or viramidine, with a cytokine, such as interferon alfa-2b (or interferon alfa-2a or pegilated alfa 2b) for the treatment of chronic infection sustained by HVC. It is considered in fact that ribavirin monophosphate and similar derivatives inhibit the synthesis and the intracellular concentration of guanosine monophosphate, while the triphosphate salt interferes with mRNA-guanylyl transferase. As in the referred cases, the viral transmission occurs generally by interaction of surface receptors present on the wall of the host cell, mainly glycans containing SA and HA glycoprotein, so that scientists are now concentrating their efforts on this typical mechanism in order to modify or to interrupt this transmission process of viral replication.

A similar mechanism also governs flavivivrus replication, with the difference that it seems that the surface receptors of host cells are several and not completely identified. However, also for flavivirus the molecular interaction between the surface of the virion and the receptor of the host cell is the first stage of the infection. This characteristic is common to viral species and to a specific cellular tropism, and to virulence as well. In fact the cellular receptors for some virus have been defined and present distinct strategies of viral adhesion, which varies from the binding specific proteins of cellular surface to the interaction with radicals of carbohydrates largely present in the host cells, such as sialic acid and heparan sulphate.

For a large number of virus specific receptors of the host cells have not been identified. The use of multiple receptors into the specific cells or topologically different can be the reason of this missed knowledge. The same mechanism has been in fact proposed for the binding system of flavivirus (31). Several flaviviruses replicate in the cells of the vertebrates and of arthropods and show a large variety and tissue tropism. Many potential-candidate receptor proteins with a molecular mass from 40 to 80 kDa, have been associated with flaviviruses in the interaction tests (32)(33)(34)(35)(36). Moreover an important role of heparan sulphate has been evidenced in the binding of Dengue-2 virus to the vertebrates cell (31).

It is very intriguing how the glucosamineglycans (GAGs) are used also by other viruses as interaction molecules during a process concentrating the viral particles on the cellular surface, to prepare the next binding to high affinity receptors (37).

However, nowadays there is no experimental test assessing function and nature of a highly affinity receptor for each flavivirus does. The binding of flavivirus and the subsequent internalization are mediated by E protein (~50 kDa), which is the main glycoproteic particle of flaviviruses (for the review, see publications by Chambers T. J. et al. (38) and by Monath T. P. et al. (39). Protein E forms an oligomer with the little protein M (8 kDa) of the membrane and it constitutes a major part of the available surface of virion. The above determines that protein E constitutes essentially the antigen target to neutralize the virus and protective antibodies. In this connection see the aforsaid publication by Monath T. P. et al. "*Flaviviruses.*" (39).

The definition of crystalline structure of ectodominium of protein E of flavivivus of viral encephalitis caused by ticks (TBE) (40) in combination with the phenotype analyses of protein E variations, has clarified the functional domains and the mechanisms involved in the binding and internalization of flaviviruses (see also the afordaid publication by Monath T. P. et al. "*Flaviviruses.*" (39).

A search for the genotypic changes associated with the arrangement to the host cell of encephalic flavivirus Murray Valley encephalitis virus (MVE) has suggested an important role of residue 390 of E protein on cellular tropism and virulence (41). The 390 Asp found in the prototype virus has been modified in the His, Gly, Ala, or Asn after passage of MVE on a cellular line of human adenocarcinoma (SW13), thus producing an growth increase in the human cellular line and thus also an attenuation of the virulence in the mouse. The 390 residue in the E protein of MVE is part of the sequence Arg-Gly-Asp (RGD), which is an important binding element of integrin in the external extra-cellular matrix and in the cell-cell adhesion (42).

This evidence has supported the first hypothesis of the location of the binding site of flavivirus receptor into a well protected and hydrophilic dominum, comprising the 390 residue, with a possible involvement of integrins in the binding of some flaviviruses (42). Moreover, the element RDG is not traceable inside the E protein of all flaviviruses: it is traceable in the Japanese encephalitis virus (JEV) (43), yellow fever virus (YFV) strain 17D (44) and in the related sequences RGE/T in other members of complex serum JEV (45)(46) (47), but the corresponding aminoacids in E protein of Dengue virus have not been related (48)(49)(50) and deleted into TBE (51). It is intriguing how RGD sequence in the vaccine 17D strains of YFV (46) appears as a consequence of the adaptation of the host cell of virulent Asibi variety, which is presenting the corresponding aminoacids Thr-Gly-Asp (52).

On the basis of the above comparisons of the sequences, it does not appear that integrins represent a general attachment type binding flaviviruses, in contrast with foot-and-mouth disease virus (53)(54) and of coxsackievirus (55), which show a closed dependence by the binding integrin RGD-mediated to entry into the host cell.

The crystalline structure of E protein of TBE specifically evidences a function in the binding receptor of the hydrophilic region which protects RGD of some flaviviruses. This sequence is located in a ring exposed to solvent (FG) placed in the immunoglobulin-like dominion III of E protein and the mutations which are involving the tropism of host cell and the virulence in the different flaviviruses are placed in this region (56).

In fact, some authors have observed that by introducing substitutions into RDG moiety in MVE with the use of an infective clone, the dominion binding the receptor in the putative flavivirus produces in mice effects into the viral growth, adhesion and internalization to the cultural cells and virulence. To have a better bibliographic overview on this subject, many other publications can be consulted (56)(33) (57)(58)(59).

Finally, HCV is one of major concern since it is believed as a major human pathogen, infecting an estimated 170 million persons worldwide—roughly five times the number infected by human immunodeficiency virus type 1. A substantial fraction of these HCV infected individuals develop 10 serious progressive liver disease, including cirrhosis and hepatocellular carcinoma. Presently, the most effective HCV therapy employs a combination of alphainterferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and long-felt need to develop also effective therapeutics for treatment of HCV infection.

General

The main embodiment of the invention is to make available a new class of compounds which show a remarkable inhibitory effect on viruses, particularly on influenza virus, hepatitis virus and other viruses responsible for serious viral diseases, particularly those where sialic acid (SA) is involved, such as for example those sustained by flaviviruses. The new compounds exert a combined and selective inhibition of enzymatic proteins of the viral envelope, such as HA, and of structural viral proteins, such as $M_2$ proteins, and glycolytic enzymes, such as NA, more particularly exhibit an interference with viral and bacterial neuraminidases and of many other micro-organisms which effect humans and animals. Furthermore the new compounds of the invention are believed also to elicit an inhibitory activity on hepatitis virus type C (HVC) and on various types of flaviviruses.

Another desired embodiment of the invention is that to provide improved and less expensive inhibitors of the replication and of transmission processes of the most common viruses responsible for serious infections, without presenting a cross resistance to the commonly used antivirals. It is another further aim of the invention to provide improved methods for the administration of new inhibitors of the invention and the rational combinations with other known antiviral agents. An additional aspect is to provide pharmaceutical compositions useful in the above embodiments. The above and further objectives will be more evident to the expert in the art field from the evaluation of the invention in whole.

While compounds which are effective to inhibit the viral functions containing a moiety of an adamantane derivative (the interference with the $M_2$ protein typically present only in influenza virus type A is elicited) and/or of ribavirin (either inducing mutations in RNA-dependent replication or inhibiting certain viral RNA-dependent RNA polymerases) are those described in WO 2008/090151, novel compounds designed to elicit in combination and synergism a further inhibition of the functions of hemagglutinin (HA) and/or neuraminidase (NA), often present in viruses, bacteria and protozoa, are particularly desired so that authors have further investigated this unexplored research field by arriving to surprising and unexpected results.

BRIEF DESCRIPTION OF THE INVENTION

In its first aspect the present disclosure provides a compound of formula (I), as indicated hereby:

(I)

wherein in the chemical structure of general formula (I):
X denotes a link —O— or —$CH_2$—; and
R denotes —H or a linear or branched $C_{1-4}$ alkyl group;
$R^1$ denotes —$(NH)_n$—$(CH_2)_m$-(T), wherein in independent way n=1 or 2 and m=0, 1, 2, 3 and 4, —NH—CO—NH-(T) or —NH—C(NH)—NH-(T), wherein the moiety -(T), is denoted from a ring having any of the following structures:

-(T-1)

wherein in the chemical structure of moiety -(T-1):
$R^5$ denotes any of —H, —$CH_3$, —$C_2H_5$, —CH—$(C_2H_5)_2$; and
$R^6$ denotes any of —NH—CO—$CH_3$, —NH—CO—$C_2H_5$; and —$R^7$ denotes —O—CH—$(CH_3)_2$, —O—CH—$(C_2H_5)_2$;

-(T-2)

-(T-3)

-(T-4)

wherein in the chemical structure of moiety -(T-4):
Z denotes —H, —CH—$(C_2H_5)_2$, —CO—$(CH_2)_6$—$CH_3$ $R^2$ denotes —OH, —$NH_2$, —O—CH—$(C_2H_5)_2$, —NH—CO—$CH_3$, —NH—CO—$CH_2$—OH, —NH—CO—$C_2H_5$, —NH—C(NH)$NH_2$; wherein optionally only one terminal hydrogen of any of those preceeding moieties $R^2$ may be substituted by a moiety -(T) or —(W) or by a moiety of another known antiviral, antibacterial or antiprotozoarian compound, with the proviso that no hydrogen of $R^3$ shall be substituted by any moiety; and $R^3$ denotes —OH, —$NH_2$, —NH—CO—$CH_3$, —NH—CO—$CH_2$—OH, —NH—CO—$C_2H_5$, or —NH—C(NH)$NH_2$; wherein optionally only one terminal hydrogen of any of those preceeding moieties $R^3$ may be substituted by a moiety -(T) or -(W) or by a moiety of another known antiviral antibacterial or antiprotozoarian compound, with the proviso that no hydrogen of $R^2$ shall be substituted by any moieties; and $R^4$ denotes —CHOH—CHOH—$CH_2$—OH, —(W), —CHOH—$CH_2$—(W) or —$CH_2$—(W), wherein the moiety —(W), is denoted from a ring having any of the following structures:

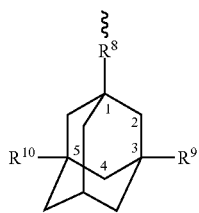

-(W-1)

wherein in the chemical structure of moiety —(W-1):

$R^8$ denotes the linking function:
—NH—, —CH$_2$—NH—, —CH(CH$_3$)—NH—,
—NH—CH(CH$_3$)—NH—, —C(CH$_3$)$_2$—CH$_2$—NH—,
—NH—CO—CH$_2$—O—CH$_2$—CH$_2$—NH— or

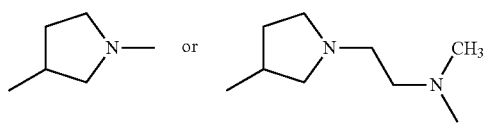

$R^9$ denotes —H, —CH$_3$ or —C$_2$H$_5$; and
$R^{10}$ denotes —H, —CH$_3$ or —C$_2$H$_5$; or

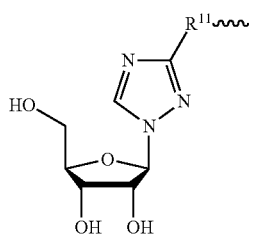

-(W-2)

wherein in the chemical structure of moiety —(W-2):
$R^{11}$ denotes the linking function:
—NH—, —CO—NH— or —C(NH)—NH—;

and their linear or branched C$_{1-4}$ carboxy mono or poly esters, addition salts, solvates, resolved enantiomers and purified diastereoisomers of the compounds of the invention.

Also encompassed within the present invention are pharmaceutical compositions containing a compound of the invention either alone or in combination with one or more compounds of the invention or with other active agents in a pharmaceutically acceptable carrier suitable for administration to mammals, particularly to humans.

In another embodiment of the invention the activity of hemagglutinin and/or neuraminidase and/or M$_2$ protein may be inhibited by a method comprising the step of treating a sample suspected of containing hemagglutinin and/or neuraminidase and/or protein M$_2$ with a compound or composition of the invention.

Another aspect of the invention provides a method for the treatment, or prevention of viral infections, for example caused by influenza virus of hepatitis virus, in a host comprising administration to the host by any suitable administration route of a therapeutically effective dose of a compound according to then invention described herein.

Moreover in another embodiment the compound of the invention shows activity also against other micro-organisms, thus it is very useful to treat the mixed infections sustained by bacteria and viruses, but also to treat other viral pathologies for which flaviviruses are responsible, and it shows a potential activity also versus other monocellular micro-organisms and protozoa which use the same mechanism for infracting the host cell of mammals In other embodiments of the present invention, novel methods for the synthesis of the compounds of this invention are also provided.

DETAILED DESCRIPTION OF THE INVENTION

The present invention purposely excludes those compounds currently known which can occasionally result from some of their combinations, but are considered embodiments and falling within the scope of the invention those compounds containing moieties of molecules which are already known to exert a certain viral activity and also those methods using as intermediate already known compound or moiety thereof.

The present invention relates to compounds of structural formula (I) of the following configuration:

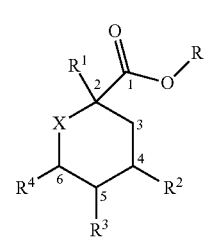

(I)

wherein:
X denotes a link —O— or —CH$_2$—; and
R denotes —H or a linear or branched C$_{1-4}$ alkyl group;
$R^1$ denotes —(NH)$_n$—(CH$_2$)$_m$-(T), wherein in independent way n=1 or 2 and m=0, 1, 2, 3 and 4, —NH—CO—NH-(T) or —NH—C(NH)—NH-(T), wherein the moiety -(T), is denoted from a ring having any of the following structures:

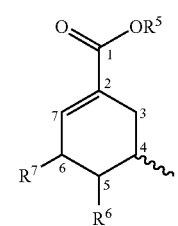

-(T-1)

wherein in the chemical structure moiety -(T-1):
$R^5$ denotes —H, —CH$_3$, —C$_2$H$_5$, —CH—(C$_2$H$_5$)$_2$; and
$R^6$ denotes —NH—CO—CH$_3$, —NH—CO—C$_2$H$_5$; and
$R^7$ denotes —O—CH—(CH$_3$)$_2$, —O—CH—(C$_2$H$_5$)$_2$;

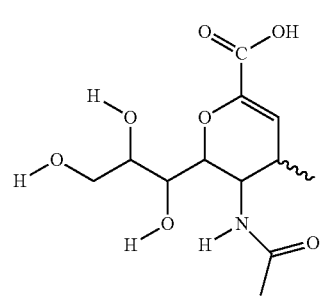

-(T-2)

wherein in the chemical structure of moiety -(T-4):

Z denotes —H, —CH—(C$_2$H$_5$)$_2$, —CO—(CH$_2$)$_6$—CH$_3$

R$^2$ denotes —OH, —NH$_2$, —O—CH—(C$_2$H$_5$)$_2$, —NH—CO—CH$_3$, —NH—CO—CH$_2$—OH, —NH—CO—C$_2$H$_5$, —NH—C(NH)NH$_2$; wherein optionally one terminal hydrogen of any of those preceeding moieties R$^2$ may be substituted by a moiety -(T) or —(W) or by a moiety of another known antiviral, antibacterial or antiprotozoarian compound, with the proviso that no hydrogen of R$^3$ shall be substituted by any moiety; and R$^3$ denotes —OH, —NH$_2$, —NH—CO—CH$_3$, —NH—CO—CH$_2$—OH, —NH—CO—C$_2$H$_5$, or —NH—C(NH)NH$_2$; wherein optionally one terminal hydrogen of any of those preceeding moieties R$^3$ may be substituted by a moiety -(T) or —(W) or by a moiety of another known antiviral, antibacterial or antiprotozoarian compound, with the proviso that no hydrogen of R$^2$ shall be substituted by any moiety; and R$^4$ denotes —CHOH—CHOH—CH$_2$—OH, —(W), —CHOH—CH$_2$—(W) or —CH$_2$—(W), wherein the moiety —(W), is denoted from a ring having any of the following chemical structures:

wherein in the chemical structure of moiety —(W-1):

R$^8$ denotes the linking function:

—NH—, —CH$_2$—NH—, —CH(CH$_3$)—NH—, —NH—CH(CH$_3$)—NH—, —C(CH$_3$)$_2$—CH$_2$—NH—, —NH—CO—CH$_2$—O—CH$_2$—CH$_2$—NH— or

R$^9$ denotes —H, —CH$_3$ or —C$_2$H$_5$; and

R$^{10}$ denotes —H, —CH$_3$ or —C$_2$H$_5$; or wherein in the chemical structure of moiety —(W-2):

R$^{11}$ denotes the linking function:

—NH—, —CO—NH— or —C(NH)—NH—;

and their linear or branched C$_{1-4}$ carboxy mono or poly esters, addition salts, solvates, resolved enantiomers and purified diastereoisomers of the compounds of the invention.

In a preferred embodiment X of the main ring of general formula (I) is denoted by —O—, typical of the sialic acid ring, or by —CH$_2$—, being preferable the linker —O— because the resulting sialochimeric compound shows better affinity with sialic acid of sialylated glycans of cellular membrane of host cell, which interacts the glycoprotein hemagglutinin (HA) and the viral, bacterial or protozoal neuraminidase (NA).

In another typical embodiment R denotes —H so that the carboxylic group remains free to interact with other glycoproteins specific of HA and of NA. In another further alternative embodiment R denotes a linear or branched C$_{1-4}$ alkyl group, such as methyl or more typically ethyl group, because the resulting ester is easily hydrolysable and it can promptly release the free carboxylic group.

In a further preferred embodiment R$^1$ the alkylaminic group —(NH)$_n$—(CH$_2$)$_m$-(T) is typically characterized by a simple aminic moiety —NH-(T) being preferable an secondary aminic link between the the carbon atom in position 2 of the main ring and the carbon atom in position 4 of moiety -(T). Furthermore, this moiety R$^1$ is typically denoted by —NH—CO—NH-(T) or by —NH—C(NH)—NH-(T), being the moiety -(T) characterized by a ring having any of the structures better detailed hereby.

In fact, in a further preferred embodiment, -(T) denotes a pentacyclic or hexacyclic ring, which is linked to the main nucleus of general formula (I), just using any of the aminic, alkylaminic, amidic or guanidinic linking functions, as described hereinbefore, typically characterized by one of the following moieties -(T-1), -(T-2), -(T-3) and -(T-4).

In a more specific embodiment -(T) is denoted by the moiety -(T-1) having the following structural formula and moieties:

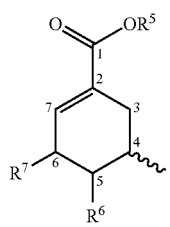

(T-1)

wherein individually, $R^5$ denotes —H or an alkyl group denoted, in order of increasing importance, —H, —CH$_3$, —CH—(C$_2$H$_5$)$_2$, or more preferably —C$_2$H$_5$, while typically $R^6$ denotes —NH—CO—CH$_3$ or —NH—CO—C$_2$H$_5$ and $R^7$ denotes —O—CH—(C$_2$H$_5$)$_2$ or —O—CH—(CH$_3$)$_2$. In the most preferred combination -(T-1) may be simultaneously when $R^5$ is —C$_2$H$_5$, $R^6$ denotes —NH—CO—CH$_3$ and $R^7$ denotes —O—CH—(C$_2$H$_5$)$_2$.

In a further embodiment -(T) denotes -(T-2), a partially substituted hexacyclic ring, typically characterized by the following structure:

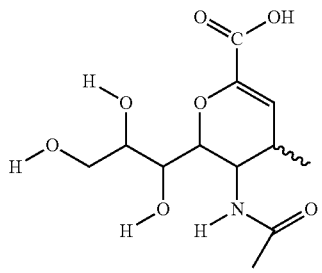

(T-2)

Also, encompassed with the present invention when -(T) denotes -(T-3), a partially substituted pentacyclic ring, typically characterized by the following structure:

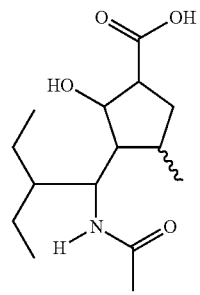

(T-3)

In another more typical embodiment -(T) denotes the partially substituted hexacyclic ring -(T-4) characterized by the following structure and subsituents:

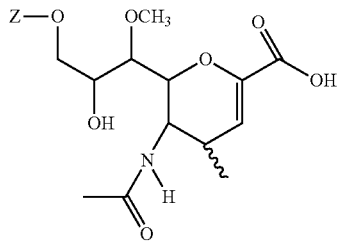

-(T-4)

wherein Z denotes an hydrogen atom (—H) or —CH—(C$_2$H$_5$)$_2$ or preferably and more typically —CO—(CH$_2$)$_6$—CH$_3$ thus being an ester.

In a further preferred combination $R^2$ denotes —OH or —NH$_2$, but also other moieties such as more preferably —NH—CO—CH$_2$—OH, —O—CH—(C$_2$H$_5$)$_2$, —NH—CO—CH$_3$, —NH—CO—C$_2$H$_5$ or —NH—C(NH)NH$_2$, being the choice correlated of the nature of the substitutions in the other nearest carbon atoms of the ring. In another typical embodiment $R^3$ denotes —NH—CO—CH$_3$ in view that this moiety is also present in SA, being the main ring of the compound of the invention a chimeric copy. Moreover it is typical that $R^3$ denotes an aminic moiety such as, but as a not limiting example, —NH$_2$, —NH—CO—CH$_2$—OH, —NH—CO—C$_2$H$_5$, —NH—C(NH)NH$_2$ or denotes an oxydrilic group —OH.

In another further typical embodiment $R^4$ denotes —CHOH—CHOH—CH$_2$—OH, but in general it is typically preferable when $R^4$ denotes a moiety of higher molecular weight, such as, but not as a limiting example, the moiety —CHOH—CH$_2$—W or —CH$_2$—W or also simply —W, wherein moiety —W is typically encompassed to have an aminic or amidic linking function binding to the main structure (I) the adamantane ring —(W-1), as typically substituted, or the ribofuranosyl-1,2,4-triazolic ring —(W-2).

A typical embodiment encompasses that —W preferably denotes an adamantan ring —W-1, showing the following structure and substituents:

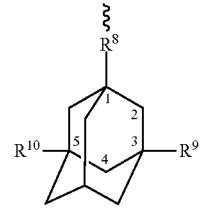

(W-1)

wherein $R^8$ typically denotes an amidic link, such as, but not as a limiting example, —NH—, —CH$_2$—NH—, —CH(CH$_3$)—NH—, —NH—CH(CH$_3$)—NH—, —C(CH$_3$)$_2$—CH$_2$—NH—, —NH—CO—CH$_2$—O—CH$_2$—CH$_2$—NH— or a cyclic aliphatic amine as for example the rings:

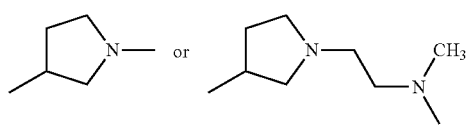

In a further typical preferable embodiment $R^9$ and $R^{10}$ of —(W-1) are symmetrically identical, and they may be —H, —CH$_3$ or —C$_2$H$_5$.

In a more preferable embodiment of the invention —(W-1) is characterized to be a specific combination where $R^8$ denotes —CH$_2$—NH— and $R^9$ and $R^{10}$ are both an hydrogen atom (—H).

In another further embodiment of the invention —W typically denotes the ribofuranosyl-1,2,4-triazolic ring —(W-2), characterized by the following structure and substituents:

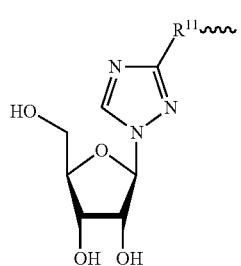
-(W-2)

wherein $R^{11}$ typically denotes a linking function such as —NH— or, as a further but not as a limiting example, —CO—NH— or —C(NH)—NH—.

Another typical embodiment is characterized by a bisubstituted compound of the invention which is characterized by the presence of the moiety -(T) encompassing the moiety -(T-1), wherein simultaneously $R^5$ denotes —$C_2H_5$, $R^6$ denotes —NH—CO—$CH_3$ and $R^7$ denotes —O—CH—$(C_2H_5)_2$, and the moiety —(W) is encompassing —(W-1), where simultaneously $R^8$ denotes —NH— and $R^9$ and $R^{10}$ are both denoted by an hydrogen atom, where additionally $R^2$ and $R^3$ are containing neither -(T) nor —(W).

In another most preferred embodiment, the physico-chemical properties of the compounds of the invention represent a remarkable improvement over the individual moieties included in the general formula (I). In fact, while the moiety —(W) is lipophilic, so that hydrochloride or other inorganic salts are generally used to improve their hydrosolubility, the compounds incorporating —(W) are soluble in water without the necessity to be transformed into a salt before use. However, the hydrosolubility makes the compounds more bioavailable both improving their absorption rate and penetration into the tissues.

In another further preferred embodiment where stronger antiviral, antibacterial or antiprotozoal effect is required, wherein $R^2$ denotes —OH or —$NH_2$, but also when other moieties such as —NH—CO—$CH_2$—OH, —O—CH—$(C_2H_5)_2$, —NH—CO—$CH_3$, —NH—CO—$CH_2$—OH, —NH—CO—$C_2H_5$ or —NH—C(NH)$NH_2$ are encompassed, optionally one terminal hydrogen of any of those preceeding moieties $R^2$ may be substituted either by the moiety -(T) or —(W) or by a moiety of another known antiviral, antibacterial or antiprotozoarian compound, with the proviso that no other hydrogen of $R^3$ shall be substituted by any moiety.

Similarly, in another further preferred embodiment, wherein $R^3$ denotes —OH or —$NH_2$, but also when other moieties such as —NH—CO—$CH_2$—OH, —O—CH—$(C_2H_5)_2$, —NH—CO—$CH_3$, —NH—CO—$CH_2$—OH, —NH—CO—$C_2H_5$ or —NH—C(NH)$NH_2$ are encompassed, optionally one terminal hydrogen of any of those preceeding moieties $R^3$ may be substituted either by the moiety -(T) or —(W) or by a moiety of another known antiviral, antibacterial or antiprotozoarian compound, with the proviso that no other hydrogen of $R^2$ shall be substituted by any moiety.

However, a skilled person understands that several other embodiments are possible, while among them the most preferred combinations are those listed in the following table.

| Compound | R | $R^1$ | $R^5$ | $R^6$ | $R^7$ | $R^2$ |
|---|---|---|---|---|---|---|
| THE 08/01 (Example 7) | —H | —NH—(T-1) | —$C_2H_5$ | —NH—CO—$CH_3$ | —O—CH—$(C_2H_5)_2$ | —OH |
| THE 10/01 (Example 8) | —H | —NH—C(NH)—NH—(T-2) | — | — | — | —OH |
| THE 10/04 (Example 12) | —H | —NH—(T-1) | —$C_2H_5$ | —NH—CO—$CH_3$ | —O—CH—$(C_2H_5)_2$ | —OH |
| THE 10/05 (Example 13) | —H | —NH—C(NH)—NH—(T-2) | — | — | — | —OH |
| THE 10/09 (Example 16) | —H | —NH—(T-1) | —$C_2H_5$ | —NH—CO—$CH_3$ | —O—CH—$(C_2H_5)_2$ | —OH |
| THE 10/01 (Example 16) | —H | —NH—C(NH)—NH—(T-2) | — | — | — | —OH |

| Compound follows | $R^3$ | $R^4$ | $R^8$ | $R^9$ | $R^{10}$ | $R^{11}$ |
|---|---|---|---|---|---|---|
| THE 08/01 (Example 7) | —NH—CO—$CH_3$ | -(W-1) | —NH— | — | — | — |
| THE 10/01 (Example 8) | —NH—CO—$CH_3$ | -(W-1) | —NH— | — | — | — |
| THE 10/04 (Example 12) | —NH—CO—$CH_3$ | -(W-1) | —CH($CH_3$)—NH— | — | — | — |
| THE 10/05 (Example 13) | —NH—CO—$CH_3$ | -(W-1) | —CH($CH_3$)—NH— | — | — | — |
| THE 10/09 (Example 16) | —NH—CO—$CH_3$ | -(W-2) | — | — | — | —CO—NH— |
| THE 10/01 (Example 16) | —NH—CO—$CH_3$ | -(W-2) | — | — | — | —CO—NH— |

Surprisingly, in another typical embodiment of the invention, the activity of hemagglutinin and/or of neuraminidase and/or of the $M_2$ protein ion-channel may be inhibited or blocked by treating a viral sample, suspected of containing hemagglutinin and/or neuraminidase and/or $M_2$ protein with a compound or a composition of the invention as described herein.

In another aspect the invention is directed to a method for the treatment or prophylaxis of viral infections, particularly from influenza A and B or of from flavivirus, more particularly from HCV, infections, in a mammalian host comprising administration to the host by any suitable administration route of a therapeutically effective dose of a compound according to the invention. However, unexpectedly and surprisingly a compound or a composition of the invention, due to its sialomimetic activity, may inhibit or block also in other micro-organisms, particularly bacteria and protozoa both the glycoproteic enzyme hemagglutinin and also neuraminidase, in view that for the adhesion and internalization into the target host cell the linking to the sialic acid of peptidoglycans on the membrane of target cell is required.

In another embodiment, novel general methods for the synthesis of the compounds of this invention are also provided.

A number of exemplary methods for the preparation intermediates for the preparation of the compounds of the invention are already known to a skilled person, but they are reported below for better convenience but they are not matter of this invention. By contrast, additional exemplary methods for the preparation of the compounds of the invention are provided below, but they are not intended to limit the scope of applicable methods. Generally, the reaction conditions such as temperature, reaction time, solvents, work up procedures, and the like, will be those common in the art for the particular reaction to be performed. The cited reference material, together with material cited herein, contains detailed descriptions of such conditions. As an exemplary method, the indicated method may be also applicable as a general synthesis for the compounds of the invention. Nevertheless, a skilled artisan would recognise that other standard procedures are available and may be used to yield the same materials.

Also encompassed within the present invention are pharmaceutical compositions containing a compound according to the invention either alone or in combination with, for example, another compound of the invention or one or more active agents in a pharmaceutically acceptable carrier thus rendering them suitable, for example, for administration to mammals. A further aspect of the present invention comprises a method for the treatment or prophylaxis of said viral, bacterial and mixed, or protozoarian diseases or conditions by combining a treatment of mammals using a compound or of a pharmaceutical composition of the invention or a mixture thereof together with a simultaneous or alternate treatment with another therapeutically effective dose of an active agent also capable of inhibiting such viral, bacterial and protozoarian infections.

The compounds of the invention also encompass enriched or resolved optical isomers at any or all asymmetric atoms. Both racemic and diastereomeric mixtures, as well as the individual optical isomers isolated or synthesized, substantially free of their enantiomeric it disctereoimeric partners, are all within the scope of the invention. The racemic mixtures may be separated into their individual optical isomers, almost pure, by using current and known techniques, such as the separation of diasteromeric salts obtained from their optically active forms, such as acids or bases, with the further reconversion to optically active substances. In many cases, the desired optical isomer is synthesized by stereospecific reactions, which start from using suitable stereoisomers of the desired starting material.

The compositions of the invention optionally comprise salts of the referred compounds herein, especially pharmaceutically acceptable non-toxic salts containing for example inorganic or preferably organic acids or bases. Salification is a preferred procedure when water soluble salts of the compounds are required either to improve the stability or the physical characteristics of the compounds of the invention.

Another aspect of the invention refers the methods to inhibit particularly the activity of hemagglutinin and of neuraminidase and, in a different extent, also concomitantly to affect $M_2$ protein and/or RNA-polymerases and/or the RNA-dependent replication, which comprises the phase of treating a sample suspected to contain hemagglutinin and/or neuraminidase and/or $M_2$ protein and/or RNA-polymerases with a compound of the invention.

The compounds of the invention are believed to act concomitantly as inhibitors of hemagglutinin and neuraminidase. However, they are also inhibitors of $M_2$ protein and of RNA-polymerases. In fact, the inhibitors will bind to locations on the surface or in the cavities of hemagglutinin, neuraminidase, $M_2$ protein and of RNA-polymerases in view of their unique chimeric geometry which can either attract or fit with one or more or those inhibitors or elicit a concomitant inhibition, as reported hereby.

In fact, it is likely that the new inhibitors will be binding those sites of the surface or of the cavities of hemagglutinin and/or of neuraminidase and/or of $M_2$ protein and/or RNA-polymerases, in view that their similar structures engage and/or compete with the referred infecting glycoproteins. However, compounds binding hemagglutinin, neuraminidase, $M_2$ protein and RNA-polymerases may bind the specific enzyme and/or glycoproteins with varying degrees of affinity and reversibility. Those compounds binding substantially irreversibly the infecting enzymes and/or glycoproteins are ideal candidates for use in the method of the invention.

The infecting organisms containing hemagglutinin and neuraminidase include bacteria (*Haemophilus influentiae, Streptococcus pneumoniae, Vibrio cholerae, Clostridium perfringens*, e *Arthrobacter sialophilus*) and viruses, especially orthomyxovirus or paramyxovirus such as influenza virus A and B type, parainfluenza virus, rhinovirus, coronavirus, flavivirus (HVC and those responsible of yellow fever and Dengue fever), mutant coronavirus and/or modified coronavirus, polyomavirus, parotitis virus, Newcastle disease virus, fowl plague virus, and Sendai virus and at least monocellular parasites, such as that of malaria and tripanosomiasis. Concomitant inhibition of hemagglutinin or of neuraminidase activity obtained from or found within any of these organisms is within the scope of the invention. As a further aspect of this invention is that some screened compounds substantially inhibit also influenza virus type A neuraminidase- and also oseltamivir-resistant strains, so making surprisingly unique those compounds of this invention.

The compounds of this invention are also useful in the treatment or prevention of such infections in birds, e.g. such as duck and goose, in mammals, such as rodents, pigs and in man.

In a further embodiment, compounds of the invention screened for inhibitory activity against viral, bacterial and protozoarian hemagglutinin and/or neuraminidase by conventional techniques for evaluating such enzymatic activity. Within the context of the invention, typically compounds are firstly screened for inhibition of hemagglutinin and neuraminidases in vitro.

A further aspect of the invention relates to methods of blocking the influx of H+ ions through the M2-protein ionchannel, inhibiting uncoating and release of free ribonucleoproteins into the cytoplasm, comprising the step of treating with a compound of the invention a sample suspected of containing M2-protein, such as strain A influenza virus. In fact, compounds of the invention are also believed to act by blocking the viral M2-protein functions. Another further aspect of the invention relates to methods of inhibiting the synthesis of guanosine monophosphate and the RNAmguanilyltransferase comprising blocking the RNAm and RNA polymerase synthesis of HVC by treating the suspected sample with a compound of the invention.

In another preferred embodiment, compounds of the invention are believed to act simultaneously as inhibitors of hemagglutinin and/or neuraminidase and/or of $M_2$ protonic ionic channel and/or RNA-polymerase synthesis. Similarly the same inhibitory effect is shown in hemagglutinin and/or neuraminidase and/or viral M2-protein and/or RNA-polymerase synthesis which is exposed also by monocellular parasites, as malaria.

In order to confirm the surprising antiviral activity, including the surprising activity on oseltamivir-resistant strains, the results of separate screenings in vitro versus influenza virus type A and type B activity of the compounds of Example 7 and Example 8 of the invention, labeled with the code THE 08/01 and THE 10/01 respectively, have been abstracted herebelow.

Studies design (I)—Influenza virus type A and type B

Antiviral activity screenings of the compounds THE 08/01 and THE 10/01 against strains of A/H1N1 and of A/H3N2 and one of type B influenza viruses have been carried out separately.

Materials and Methods

1. Propagation and Titration of Influenza Virus Strains

The strains of influenza virus A/H3N2 (A/Panama/2007/99), A/H1N1 (A/New Caledonia/20/99) and B (B/Parma/1/07) have been spread into permissive cellular lines MDCK (Madin-Darby Canine Kidney).

Briefly, the influenza viruses have been inoculated on a confluent monolayer of MDCK cells and incubated at 37° C., 5% $CO_2$, during 5 days. The surnatant has been thus collected and titred. The assay determinations have been carried out by the plaque formation test (Plaque Assay, Pa.).

More particularly, serial dilutions on base 10 of each isolate have been inoculated on a confluent MDCK monolayers in 12 wells plates. After incubation for 1 hour at 37° C., 5% $CO_2$, the viral inoculate was removed and the infection medium (MEM (Minimum Essential Medium) containing 10 μg/ml trypsin, 2% agar) has been added. After incubation during three days at 37° C., 5% $CO_2$, the cellular monolayers have been fixed with a solution of glutaraldehyde 5% and, after agar removal, have been coloured with a 5% carbol-fuchsin solution. The plaques have been visually counted and the assay of the isolate has been expressed as plaque forming unit (Plaque Forming Unit, PFU) per ml (PFU/ml).

2. Evaluation of Antiviral Activity 2.1. Preparation of the Compounds Under Analysis Each of the compounds THE 08/01 (compound of Example 7) and THE 10/01 (compound of Example 8) have been suitably reconstituted in sterile distilled water at a concentration of 100 mM.

Then, serial dilutions, on base 10, for each compound under test in an interval from 0.01 μM to 100 μM have been prepared.

2.2. Plaque Reduction Assay (PRA)

Confluent monolayers of MDCK cells, grown in 12 wells plaques ($10^5$ cells/ml) for each compound under testing, have been infected with about 50 PFU/ml (PFU=Paque Forming Unit) of each viral isolate (A/H3N2, A/H1N1 and B). After 1 h incubation at 37° C., 5% $CO_2$, to enhance the viral absorption, the viral inoculate has been removed and the cellular monolayers have been washed twice by a MEM culture media. An overlay-medium (10 μg/ml trypsin, 2% agar in MEM) has been added to each well containing serial dilutions (interval: 0.01 μM-100 μM) of the compounds under analyses. The test has been carried out in duplicate and simultaneously a reaction control not containing the antiviral compound has been prepared. The cultures has been incubated at 37° C., 5% $CO_2$, during 3 days. After, the cellular monolayers have been fixed by using a 5% glutaraldehyde and incubated for at least 3 hours at room temperature to enhance the penetration into agar. After agar removing, the cellular monolayers have been coloured by a 5% carbol-fuchsin solution.

The plaques have been visually counted and the plaques inhibition degree has been calculated in relation to controls not containing the compounds under testing. Thus the concentration of each compound able to reduce the 50% plaques number versus the control without the compound (EC50) has been determined. For this reason dose-response curves have been constructed by the GraphPad Prism biostatistic software.

3. Results

THE 08/01 and THE 10/01 have demonstrated antiviral activity versus the tested influenza virus type A and B. The dose-response curves of the compounds THE 08/01 and THE 10/01 versus the tested influenza viruses are represented from sigmoidal functions, while the curves allow to extrapolate the EC50, and the relevant confidence intervals (95% CI). As exemplary presentation the sigmoidal functions of THE 08/01 are reported in FIGS. 1, 2 and 3. Particularly, EC50 are reported hereby:

EC50 THE 08/01 vs A/H1N1: 9.9 μM (95% CI: 4.5-21.5 μM);

EC50 THE 08/01 vs A/H3N2: 15.4 μM (95% CI: 2.5-95.8 μM);

EC50 THE 08/01 vs B: 125.5 μM (95% CI: 7.8-2014.0 μM); and

EC50 THE 10/01 vs A/H1N1: 11.7 μM (95% CI: 7.3-29.8 μM);

EC50 THE 10/01 vs A/H3N2: 18.3 μM (95% CI: 9.6-83.2.8 μM);

EC50 THE 10/01 vs B: 99.5 μM (95% CI: 11.4-1937.6 μM); and

4. Conclusions

The results obtained by the performed tests allow to issue the following considerations: THE 08/01 has shown antiviral activity both versus influenza viruses type A and B. The antiviral activity is resulted 10 folds more higher versus virus type A than that of virus type B.

Similar results have been achieved with THE 10/01.

Study design (II)—Influenza virus A/H1N1(H275Y) (oseltamivir-resistant) Evaluation in vitro of the antiviral activity of the compound THE 08/01 against influenza virus type A subtype H1N1 presenting the mutation H275Y in the gene encoding neuraminidase-A/H1N1(H275Y).

The anti-influenza activity of the compound THE 08/01 has been determined on an isolate of influenza virus A/H1N1 (H275Y) and on a non mutated influenza virus A/H1N1.

Materials and Methods

1. Propagation and Titration of the Influenza Viruses

The strains of influenza virus A/H1N1(H275Y) (A/Parma/38/2008) and A/H1N1 (A/New Caledonia/20/1999) have been spread on embryonic chicken-eggs. in short, the influenza virus strain have been inoculated, by allantoyc route, in chicken eggs and incubated at 37° C. during tree days, and the allantoic liquid has been hence collected and titrated.

The determination of the assay has been carried out by plaque formation test (Plaque Assay, Pa.). Particularly, serial dilutions on base 10 of each viral isolate have been inoculated on a confluent monolayer of permissive cells MDCK (Madin-Darby Canine Kidney) in plates with 12 wells. After incubation during 1 hour at 37° C., 5% $CO_2$, the cellular inoculate has been removed and the infection medium (MEM containing 10 μg/ml TPCK-trypsin, 2% agar) has been added. After incubating during 3 days at 37° C., 5% $CO_2$, the cellular monolayers have been fixed with a solution of glutaraldehyde 5% and, after agar removal, have been colored with a solution of 5% carbol-fuchsin.

The plaques have been visually counted and the assay of the isolate has been expressed as plaque forming unit (Plaque Forming Unit, PFU) per ml (PFU/ml).

2. Evaluation of the Antiviral Activity of the Compound Under Testing 2.1 Preparation of the Compound Under Testing The compounds THE 08/01 has been suitably reconstituted in distilled sterile water at a concentration of 1 mM. Thereafter, serial dilutions have been prepared. on basis 10, in a range from 0.01 μM to 100 μM.

2.2. Plaque Reduction Assay (Plaque Reduction Assay, PRA) Confluent monolayers of MDCK cells, grown in plates with 12 wells ($10^5$ cells/ml), have been infected with about 50 PFU/ml of each viral isolate (A/H1N1(H275Y) and A/H1N1). After 1 hour incubation at 37° C., 5% $CO_2$ to enhance the viral absorption, the viral inoculate has been removed and the cellular monolayers have been washed twice with MEM culture media. An overlay-medium (10 μg/ml TPCK-trypsin, 2% agar in MEM) has been added to each well containing serial dilutions (range: 0.01 μM-100 μM) of the compounds under evaluation. The test has been carried out in duplicate and simultaneously a reaction control not containing the antiviral compound has been set up. The cultures have been then incubated at 37° C., 5% $CO_2$, during 3 days.

Thereafter, the cellular monolayers have been fixed by using a solution of 5% glutaraldehyde and incubated during at least 3 hours at room temperature to enhance its penetration into the agar. After removing the agar, the cellular monolayers have been colored with a 5% carbol-fuchsin solution. The plaques have been visually counted and the degree of plaques inhibition of 50% in relation to the control without the compound under testing (EC50) Therefore the concentration of compound necessary to reduce the number of plaques by 50% versus the control without the compound (EC50) has been determined. For this purpose dose-response curves have been drawn by using the GraphPad Prism biostatic software.

3. Results

THE 08/01 has shown antiviral activity in vitro versus the influenza virus A/H1N1(H275Y) comparable to that determined versus A/H1N1. The dose-response curves of the compound THE 08/01 versus the two tested influenza viruses are represented from the sigmoidal functions represented in FIG. 4. The construction of those curves has allowed to extrapolate the EC50 and the relevant confidence intervals (95% CI). More particularly:

EC50 THE 08/01 vs A/H1N1(H275Y): 14.5 μM (95% CI: 5.2-41.5 μM);

EC50 THE 08/01 vs A/H1N1: 16 μM (95% CI: 3.1-81.8 μM).

4. Conclusions

The results obtained from the performed tests allow to conclude that THE 08/01 shows comparable antiviral activity versus the isolate of influenza virus A/H1N1 and of that A/H1N1 presenting the mutation H275Y, that confers resistance to oseltamivir.

Those data therefore provide a certain evidence of an enhanced antiviral activity of the compounds of the invention over the prior art compounds. In fact, there is an enhanced antiviral activity of both tested compounds sometimes at a very low concentration so that an hypothesis of an inhibition on hemagglutinin may be envisaged. However, the unexpected activity versus type B virus, in absence of $M_2$ protein in type B virus (M2 protein is typically present only in influenza virus type A) seems supporting the hypothesis of a new mechanism of action involving concomitantly hemagglutinin and/or a $M_2$ protein inhibitions. However, since the compounds evidenced a weak activity versus strain A/H1N1-275Y (resistant to oseltamivir), it is likely that the neuraminidase inhibiting effect is also accompanied to the above mentioned activity (hemagglutinin and/or a $M_2$ protein inhibition). This should be object of further specific studies. The compounds of the present invention may be formulated with conventional carriers and excipients, which will be selected in accord with ordinary practice. Tablets will contain excipients, glidants, fillers, binders and the like. Aqueous formulations are prepared in sterile form, and when intended for delivery by other when oral administration generally will be isotonic. All formulations will optionally contain excipients such as those set forth in the reknown publication: "*Handbook of Pharmaceutical Excipients", 4.$^{th}$* Edition, Rowe R. C. et al, Pharmaceutical Press (2003). Excipients include ascorbic acid and other antioxidants, chelating agents such as EDTA, carbohydrates such as dextrin, hydroxyalkylcellulose, hydroxyalkyl-methylcellulose, stearic acid and the like. One or more compounds of the invention (hereinafter ailson referred to as the active compounds) may be administrated by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like.

It will be appreciated that the preferred route may vary with for example the condition of the recipient. An advantage of the compounds of this invention is that they are orally bioavailable and can be dosed as oral pharmaceutical forms; it is possible, but not necessary to administer them by intrapulmonary or intranasal routes. While it is possible to administer the active compound or their association thereof in the same solid form (powder) as they are obtained, it may be advisable to formulate them in a conventional pharmaceutical composition to be more conveniently administered.

The formulations of the invention, which may be both for veterinary and for human use, comprise at least one active compound of the invention, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in "Remington's Pharmaceutical Sciences" Mack Publishing Co., Easton, Pa., U.S.A. Such methods include the step of bringing into association the active ingredient with the carrier which constitutes one or more accessory ingredients. In general the formulations may be prepared by uniformly and intimately bringing into association the active ingredient with liquid carriers or finely divided solid carriers or both, and then, if necessary, shaping the product as desired. Formulations of the invention suitable for oral administration may be prepared as solid units such as capsules, cachets or tablets each containing a predetermined amount of the active ingredient; as a powder or granules; as solution or a suspension in an aqueous liquid or a nonaqueous liquid; or as an oil-in-water liquid emulsion or a water-in-oil liquid emulsion. The active ingredient may also be presented as a bolus, electuary or paste. A tablet is made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations may preferably be applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredient(s) may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, Le. an alcohol having two or more hydroxyl groups such as propylene glycol, butane 1,3-diol, mannitol, sorbitol, glycerol and polyethylene glycol (including PEG 400) and mixtures thereof. The topical formulations may also desirably include a compound which enhances absorption or penetration of the active ingredient through the skin or other affected areas. Examples of such dermal penetration enhancers include dimethyl sulphoxide and related analogs. The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fato Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of the invention include Tween® 60, Span® 80, cetostearyl alcohol, benzyl alcohol, myristyl alcohol, glyceryl mono-stearate and 30 sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain/esters known as Crodamol CAP may be used, the last three being preferred esters. These may be used alone or in combination depending on the properties required. Alternatively, high melting point lipids such as white soft paraffin are used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 2.0% w/w. Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration may be presented as a suppository with a suitable base comprising for example cocoa butter or a salicylate. Formulations suitable for intrapulmonary or nasal administration have a particle size in the range of 0.1 to 500 microns (including particle sizes in a range between 0.1 and 500 microns in increments microns such as 0.5, 1, 30 microns, 35 microns, etc.), which are administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of influenza A or B infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain antioxidants, buffers, bacteriostats and solutes which render the formulation isotonic with the blood of the intended recipient; and aqueous and nonaqueous sterile suspensions which may include suspending agents and thickening agents.

The formulations may be presented in unit-dose or multi-dose containers, for example sealed ampoules and vials, and may be stored in a freeze-dried (lyophilized) condition requiring only the addition of the sterile liquid carrier (solvents), for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient. It should be understood that in addition to the ingredients particularly mentioned above, the formulations of this invention may include other agents conventional in the art having regard to the type of formulation in question, for example those suitable for oral administration may include flavouring agents.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention may be used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

An effective dose of active compound depends at least on the nature of the condition being treated, toxicity, whether the compound is being used prophylactically (lower doses) or against an active influenza infection, the method of delivery, and the pharmaceutical formulation, and will be determined by the clinician using conventional studies at scalar doses. It can be expected to be from about 0.0001 to about 100 mg/kg body weight per day. Typically, from about 0.01 to about 10 mg/kg bodyweight per day. More typically, from about 0.01 to about 5 mg/kg body weight per day. More typically, from about 0.05 to about 0.5 mg/kg body weight per day. For example, for inhalation the daily candidate dose for an adult human of approximately 70 kg body weight will range from 1 mg to 1000 mg, preferably between 5 mg and <500 mg, and may take the form of single or multiple doses.

Larger therapeutically effective daily dosages may be also administered when required by the pathological conditions of the subject. Active compounds of the invention are also used in combination with other active ingredients. Such combinations are selected based on the condition to be treated, cross-reactivities of ingredients and pharmacoproperties of the combination. For example, when treating viral infections of the respiratory system, in particular influenza infection, the compositions of the invention are combined with anti-virals (such as amantadine, rimantadine and ribavirin), mucolytics, expectorants, bronchial dilators, antibiotics, antipyretics, or analgesics. Ordinarily, antibiotics, antipyretics, and analgesics are administered together with the compounds of the invention. The invention has been described in detail sufficient to allow one of ordinary skill in the art to make and use the subject matter of the following examples. It is apparent that certain modifications of the methods and compositions of the following examples can be made within the scope and spirit of the invention.

Figure 2:
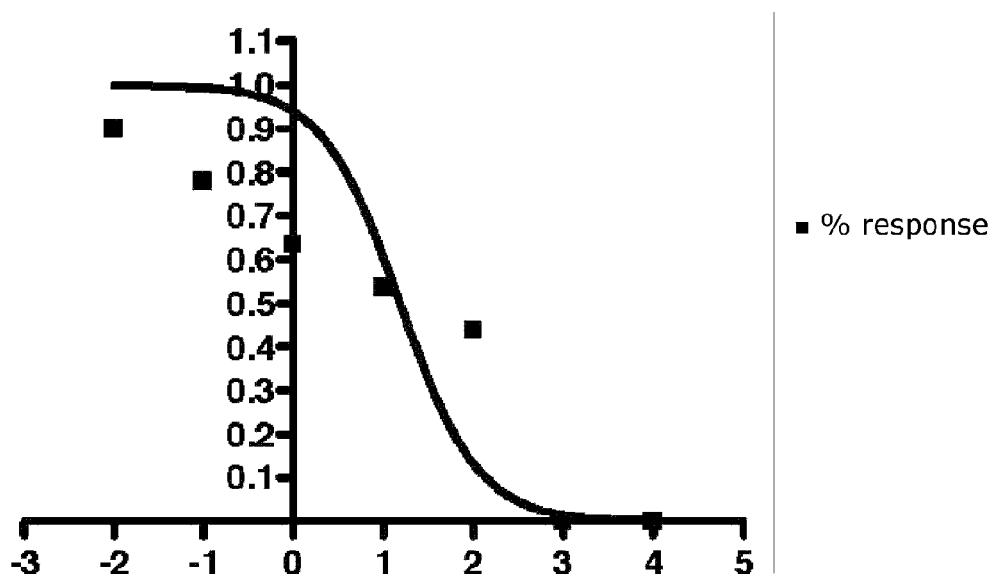
Figure 3:
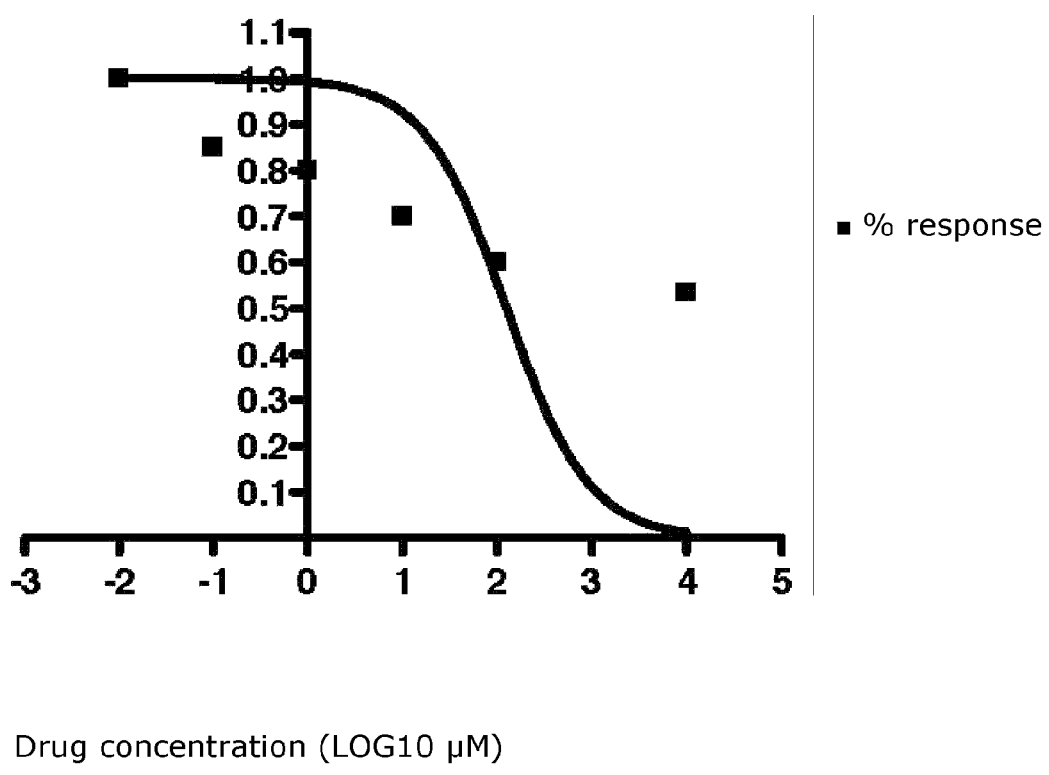

The invention will be further described with reference to the following exemplary embodiments, and accompanying FIG. 1-5 wherein:

FIG. 1—THE 08/01 vs Flu A/H1N1
FIG. 2—THE 08/01 vs Flu A/H3N2
FIG. 3—THE 08/01 VS Flu B
FIG. 4—THE 08/01 vs Flu A/H1N1(H275Y)+Flu A/H1N1
FIG. 5—Test results HCV (THE 08/01, THE 10/01, THE 10/09)

EXAMPLES

Example 1

Preparation of Methyl-beta-ketoside of Methyl ester of Neu5Ac

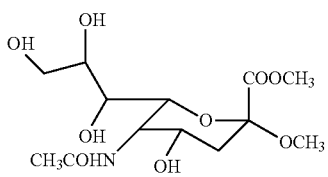

4.50 mg of sialic acid (14.55 mmol) dissolved in 350 ml of absolute ethanol were mixed to 10.0 g of Dowex 50 (H+)* resin and the suspension was refluxed during 48 hours under constant stirring. The analytical determination with resorcinol-HCl and thiobarbituric acid (TBA) showed that at 24 and 48 hours the 85% and 97% of Neu5Ac was converted into of methyl-beta-ketoside, respectively. The sample was then filtered off on current paper filter and the elute was concentrated to dryness by means of a rotary evaporator to yield an oily yellowish liquid, which was then recovered with a reduced volume of a mixture of ethyl ether:methanol (3:1 w/w) and the solution was kept standing during 24-48 hours at 4° C. The crystalline substance was recovered by filtration and dried on $P_2O_5$. Yield: 2.90 g (M.W. 337.4). The resulting compound is positive to resorcinol-HCl reaction (with the same intensity as sialic acid) and negative to TBA reaction.

(*) Preemptively the Dowex 50 (H+)* resin shall be activated with 60 ml of a solution of hydrochloric acid 1.0 M during 60 minutes at room temperature. Then the resin shall be fully washed with water and after with methanol before using.

Example 2

Preparation of Methyl-beta-ketoside of Neu5Ac by Soft Alkaline Hydrolysis Methyl-beta-ketoside of Methyl Ester of Neu5Ac

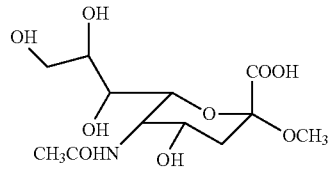

2.90 g of methyl-beta-ketoside of methyl ester of Neu5Ac (8.60 mmol) were dissolved in 200 ml of 0.06 M sodium hydroxide and under incubation at room temperature during 2.5 hours. The solution is then neutralized and deionized by passing it on a Dowex 50 (H±) resin. The elute was then lyophilized to yield a whitish solid.

Yield: 2.64 g (M.W. 332.4).

The obtained compound resulted positive to resorcinol-HCl reaction and negative to TBA reaction.

Example 3

Preparation of Methyl-Beta-Ketoside of C7-Neu5Ac

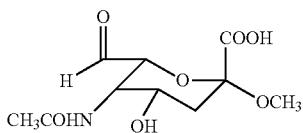

The lyophilized powder obtained by the previous phase constituted by 2.90 g of methyl-beta-ketoside of Neu5Ac (8.20 mmol) was dissolved in 100 ml of distilled water, adding 214.0 ml of $NaIO_4$ (sodium metaperiodate) 0.2 M (42.8 mmol). Molar ratio of methyl-beta-ketoside of Neu5Ac: $NaIO_4$=1: 5.24. The solution was kept during 2 hours in darkness at room temperature under constant stirring. 260.0 ml of an aqueous solution of 0.1 M barium acetate were added to the mixture to precipitate the formed iodate and the excess of periodate. The mixture was filtered using a current paper filter. The elute was saturated bubbling carbon dioxide to precipitate the excess of barium acetate and then filtered off on a paper filter. The elute was lyophilized to yield a slightly yellowish solid.

Yield: 1.806 g (M.W. 260.24) The obtained compound resulted positive to resorcinol-HCl reaction and negative to TBA reaction.

Example 4

Preparation of C7-Neu5Ac

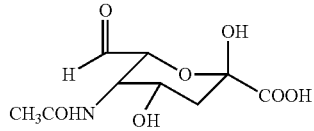

It is obtained by soft hydrolysis of methyl-beta-ketoside of C7-Neu5Ac. The lyophilized powder obtained into the previous example, corresponding to 7.0 mmol, were dissolved in 40 ml of 2.3 mM formic acid at a pH of about 4.0 and heated to 80° C. during 1 hour. The solution was then lyophilized.

Yield: 1.674 g (M.W. 246.21).

The obtained compound is positive to resorcinol-HCl reaction and negative to TBA reaction.

Example 5

Absorption of C7-Neu5Ac to DEAE-Sephadex A-25

The lyophilized powder obtained into the previous step, corresponding to 6.80 mmol, is dissolved in 200 ml of methanol:water (1:1 v/v). Then 20.0 g of DEAE-Sephadex A-25 are added and the sample is maintained under continuous stirring at 4° C. overnight. Once passed the above period, the formed complex of C7-Neu5Ac-DEAE-Sephadex A-25 is washed many times with methanol:distilled water (1:1 v/v). The complex is then dissolved in 600 ml of distilled water.

Example 6

Preparation of Amantadine-C7Neu5Ac

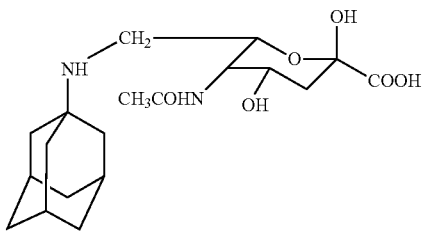

To 30.0 ml of the suspension obtained into the previous example, which containing 0.34 mmol of C7-Neu5Ac is added amantadine in an excess of 1.5 folds of sialic acid (0.51 mmol) and also 100 ml of sodium borohydride necessary to reduce the imine formed during the reaction transforming it in a stable secondary amine. The resulting sample is incubated at 4° C. under continuous stirring overnight. The gel is then washed more times with methanol:distilled water (1:1 v/v). The obtained derivative constituted by amantadine-C7-Neu5Ac is eluted by DEAE-Sephadex A-25 with a mixture of 100 ml of chloroform:methanol:NH$_4$OH 35% (60:35:8, v/v/v). The gel is maintained into incubation with this solvent mixture during 1 hour at room temperature. After the sample is centrifugated, the solid residue is discarded (DEAE-Sephadex A-25) and the supranatant, containing amantadine-C7-Nu5Ac is brought to dryness by a rotatory essiccator. The derivative is then dissolved into 100 ml of distilled water and lyophilized. The sample can be stored lyophilized.

Example 7

Preparation of Compound [Amantadine-C7-Neu5Ac—C$_{16}$H$_{28}$N$_2$O$_4$] having the Following Structural Formula

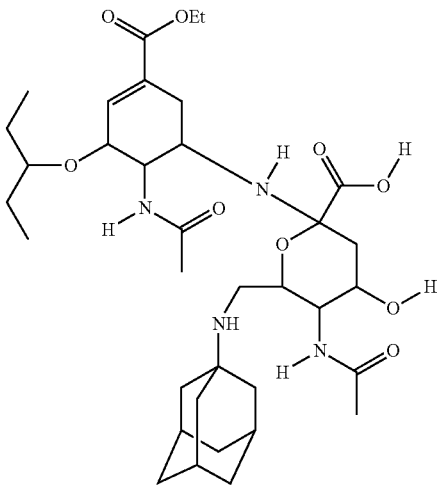 [SMILES: CCOC(=O)C1=CC(OC(CC)CC)C(NC(C)=O)C(NC2(C(=O)O)CC(O)C(NC(C)=O)C(CNC34CC5CC(CC(C5)C3)C4)O2)C1]

The compound obtained from the previous phase (amantadine-C7-Neu5Ac) is dissolved into 100.0 ml of distilled water. Afterwards the compound C$_{16}$H$_{28}$N$_2$O$_4$·PO$_4$H$_3$ {CAS [204255-11-8]; M.W. 410.4} is added in molar excess of 1.5 folds in comparison of the sialic acid content of the complex (0.51 mmol). The sample is incubated at 60° C. during 2 hours. Then NaBH$_3$CN (sodium cyanoborohydride) is added in the ratio of C$_{16}$H$_{28}$N$_2$O$_4$:NaBH$_3$CN (1:0.5; W/W) and the resulting mixture is incubated overnight at 60° C.. Afterwards 10.0 g of DEAE-Sephadex A-25 are added and the mixture is incubated under continuous stirring at 4° C. overnight and after this period the newly obtained compound amantadine-C7-Neu5Ac—C$_{16}$H$_{27}$N$_2$O$_4$-DEAE-Sephadex A-25 is washed many times with a mixture of methanol:distilled water (1:1, V/V). The derivative obtained in this way and constituted by amantadine-C7-Neu5Ac—C$_{16}$H$_{27}$N$_2$O$_4$ is eluted from DEAE-Sephadex A-25 with a mixture of 200.0 ml of chloroform:methanol:NH$_4$OH 35% (60:35:8; V/V/V).

The gel is incubated with this solvent mixture during 1 hour at room temperature. Afterwards the sample is centrifugated, the solid residue is discarded (DEAE-Sephadex A-25) and the supranatant is dried by a rotating desiccator, obtaining the compound amantadine-C7-Neu5Ac—C$_{16}$H$_{27}$N$_2$O$_4$. The compound is then recovered into a suitable volume of distilled water till complete dissolution and then lyophilized.

Store preferably the sample in freezer.

Example 8

Preparation of Compound [Amantadine-C7-Neu5Ac—C$_{12}$H$_{20}$N$_4$O$_7$] having the Following Structural Formula

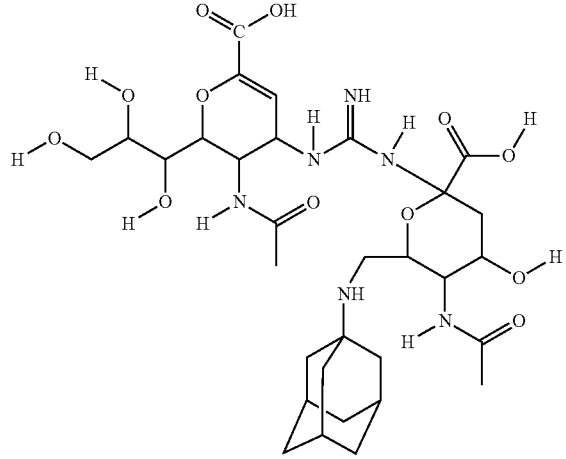 [SMILES: CC(=O)NC1C(O)CC(NC(=N)NC2C=C(C(=O)O)OC(C(O)C(O)CO)C2NC(C)=O)(C(=O)O)OC1CNC12CC3CC(CC(C3)C1)C2]

The compound obtained from the previous phase (amantadine-C7-Neu5Ac) is dissolved in 10 ml of distilled water and 2.69 g of $C_{12}H_{20}N_4O_7$ {CAS [139110-80-8]; M.W. 332.30} are added. Incubate the sample during 2 hours at 60° C. under stirring. Add 1.37 g of sodium cyanoborohydride (NaBH3CN). Incubate the sample at 60° C. under stirring overnight. Centrifugate and eliminate the supernatant. Wash at least once with 30 and 50 ml of distilled water. Centrifugate again and eliminate the supernatant. Add 50 ml of the solvent mixture chloroform:methanol:$NH_4OH$ 15 M (60:35:8; V/V/V). Incubate the sample during 1 hour at room temperature under stirring. Centrifugate, dry the supranatant into a rotating desiccator. Place the dried sample in a minimum volume of water. Lyophilize and store the sample in freezer at −20° C.

Example 9

Preparation of Compound [Amantadine-C7-Neu5Ac—$C_{15}H_{28}N_4O_4$] Having the Following Structural Formula

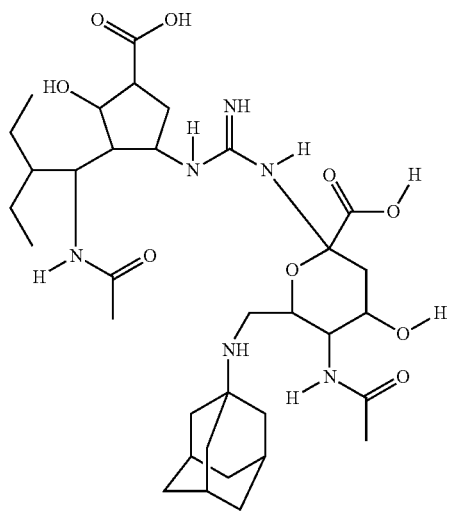 [SMILES: CCC(CC)C(CNC(C)=O)C1C(NC(=N)NC2(C(=O)O)CC(O)C(NC(C)=O)C(CNC34CC5CC(CC(C5)C3)C4)O2)CC(C(=O)O)C1O]

The compound obtained from the previous phase (amantadine-C7-Neu5Ac) is dissolved in 10 ml of distilled water and 2.66 g of $C_{15}H_{28}N_4O_4$ {CAS [229614-55-5]; M.W. 328.41} are added. Incubate the sample during 2 hours a 60° C. under stirring. Add 1.37 g of sodium cyanoborohydride (NaBH$_3$CN). Incubate the sample at 60° C. under stirring overnight. Centrifugate and eliminate the supernatant. Wash at least once with 30 and 50 ml of distilled water. Centrifugate again and eliminate the supernatant. Add 50 ml of the solvent mixture chloroform:methanol:$NH_4OH$ 15 M (60:35:8; V/V/V). Incubate the sample during 1 hour at room temperature under stirring. Centrifugate, dry the supranatant into a rotating dessicator.

Place the dried sample in a minimum volume of water. Lyophilize and store the sample in freezer at −20° C.

Example 10

Preparation of Compound [Amantadine-C7-Neu5Ac—$C_{13}H_{22}N_4O_7$] Having the Following Structural Formula

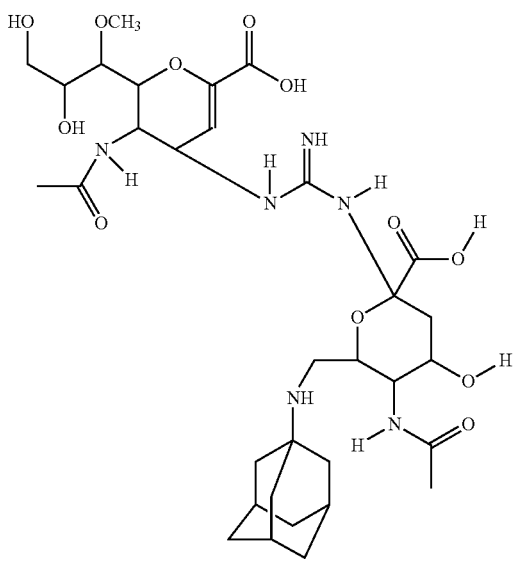 [SMILES: COC(C(O)CO)C1OC(C(=O)O)=CC(CNC(=N)NC2(C(=O)O)CC(O)C(NC(C)=O)C(CNC34CC5CC(CC(C5)C3)C4)O2)C1NC(C)=O]

The compound obtained from the previous phase (amantadine-C7-Neu5Ac) is dissolved in 10 ml of distilled water and 2.80 g of $C_{13}H_{22}N_4O_7$ {CAS [203120-17-6]; M.W. 472.53} are added. Incubate the sample during 2 hours a 60° C. under stirring. Add 1.43 g of sodium cyanoborohydride (NaBH$_3$CN). Incubate the sample at 60° C. under stirring overnight. Centrifugate and eliminate the supernatant. Wash at least once with 30 and 50 ml of distilled water. Centrifugate again and eliminate the supernatant. Add 50 ml of the solvent mixture chloroform:methanol:$NH_4OH$ 15 M (60:35:8; V/V/V). Incubate the sample during 1 hour at room temperature under stirring. Centrifugate, dry the supranatant into a rotating desiccator. Place the dried sample in a minimum volume of water. Lyophilize and store the sample in freezer at −20° C.

Example 11

Preparation of Rimantadine-C7Neu5Ac

To 61.08 ml sample obtained from Example 5 are added 10 ml of distilled water and 1.75 g of rimantadine-HCl. Incubate the samples at 4° C. under stirring overnight. The obtained imine, chemically unstable, is after reduced to a stable secondary amine, adding to each of the 6 samples 1.75 g of sodium borohydride (NaBH$_4$) and incubating the sample at room temperature, during 1 hour. Centrifugate the all samples and eliminate the supernatant. Wash at least once with 30 and 50 ml of distilled water. Centrifugate again with 30 and 50 ml of distilled water. Centrifugate again and eliminate the supernatants.

Example 12

Preparation of Compound [Rimantadine-C7-Neu5Ac—$C_{16}H_{28}N_2O_4$] Having the Following Structural Formula

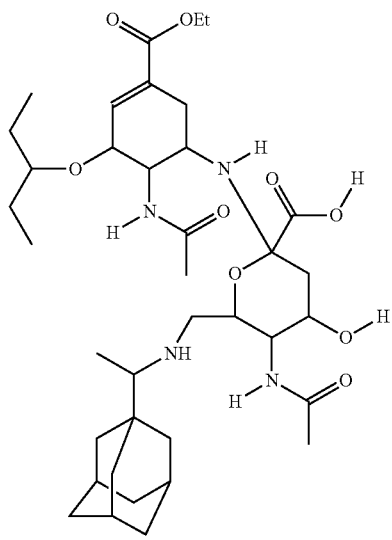 [SMILES: CCOC(=O)C1=CC(OC(CC)CC)C(NC(C)=O)C(NC2(C(=O)O)CC(O)C(NC(C)=O)C(CNC(C)C34CC5CC(CC(C5)C3)C4)O2)C1]

The compound obtained from the previous phase (rimantadine-C7-Neu5Ac) is dissolved in 10 ml of distilled water and 3.32 g of $C_{16}H_{28}N_2O_4 \cdot PO_4H_3$ {CAS [204255-11-8]; M.W. 410.4} are added. Incubate the sample during 2 hours a 60° C. under stirring. Add 1.7 g of sodium cyanoborohydride ($NaBH_3CN$). Incubate the sample at 60° C. under stirring overnight. Centrifugate and eliminate the supernatant. Wash at least once with 30 and 50 ml of distilled water. Centrifugate again and eliminate the supernatant. Add 50 ml of the solvent mixture chloroform:methanol:$NH_4OH$ 15 M (60:35:8; V/V/V). Incubate the sample during 1 hour at room temperature under stirring. Centrifugate, dry the supernatant into a rotating essiccator. Place the dried sample in a minimum volume of water. Lyophilize and store the sample in freezer at −20° C.

Example 13

Preparation of Compound [Rimantadine-C7-Neu5Ac—$C_{12}H_2O_4O_7$] Having the Following Structural Formula

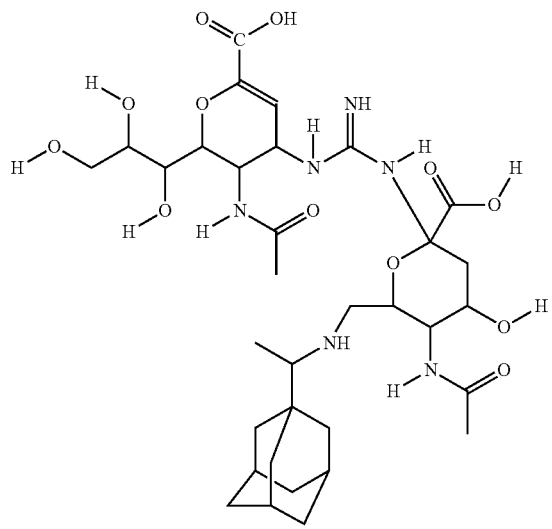 [SMILES: CC(=O)NC1C(O)CC(NC(=N)NC2C=C(C(=O)O)OC(C(O)C(O)CO)C2NC(C)=O)(C(=O)O)OC1CNC(C)C12CC3CC(CC(C3)C1)C2]

The compound obtained from the previous phase (rimantadine-C7-Neu5Ac) is dissolved in 10 ml of distilled water and 2.69 g of $C_{12}H_{20}N_4O_7$ {CAS [139110-80-8]; M.W. 332.30} are added. Incubate the sample during 2 hours a 60° C. under stirring. Add 1.37 g of sodium cyanoborohydride (NaBH3CN). Incubate the sample at 60° C. under stirring overnight. Centrifugate and eliminate the supernatant. Wash at least once with 30 and 50 ml of distilled water. Centrifugate again and eliminate the supernatant. Add 50 ml of the solvent mixture Chloroform:Methanol:$NH_4OH$ 15 M (60:35:8; V/V/V). Incubate the sample during 1 hour at room temperature under stirring. Centrifugate, dry the supernatant into a rotating desiccator. Place the dried sample in a minimum volume of water. Lyophilize and store the sample in freezer at −20° C.

Example 14

Preparation of Compound [Rimantadine-C7-Neu5Ac—$C_{15}H_{28}N_4O_4$] Having the Following Structural Formula

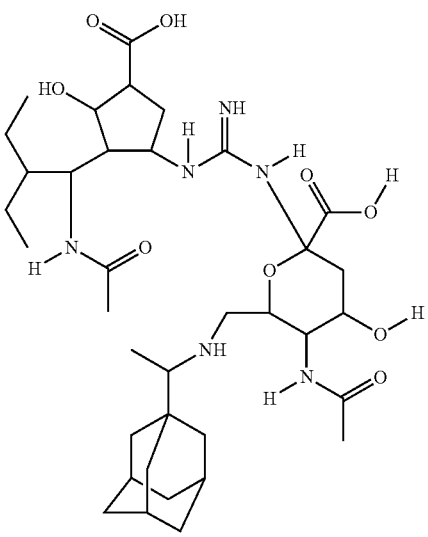 [SMILES: CCC(CC)C(CNC(C)=O)C1C(NC(=N)NC2(C(=O)O)CC(O)C(NC(C)=O)C(CNC(C)C34CC5CC(CC(C5)C3)C4)O2)CC(C(=O)O)C1O]

The compound obtained from the previous phase (rimantadine-C7-Neu5Ac) is dissolved in 10 ml of distilled water and 2.66 g of $C_{15}H_{28}N_4O_4$ {CAS [229614-55-5]; M.W. 328.41} are added. Incubate the sample during 2 hours a 60° C. under stirring. Add 1.37 g of sodium cyanoborohydride ($NaBH_3CN$). Incubate the sample at 60° C. under stirring overnight. Centrifugate and eliminate the supernatant. Wash at least once with 30 and 50 ml of distilled water. Centrifugate again and eliminate the supernatant. Add 50 ml of the solvent mixture chloroform:methanol:$NH_4OH$ 15 M (60:35:8; V/V/V). Incubate the sample during 1 hour at room temperature under stirring. Centrifugate, dry the supernatant into a rotating desiccator. Place the dried sample in a minimum volume of water. Lyophilize and store the sample in freezer at −20° C.

Example 15

Preparation of Compound [Rimantadine-C7-Neu5Ac—$C_{13}H_{22}N_4O_7$] Having the Following Structural Formula The complex obtained into the previous phase (rimantadine-C7-Neu5Ac) is dissolved in 10 ml of distilled water and 2.80 g of $C_{13}H_{22}N_4O_7$ {CAS [203120-17-6]; M.W. 472.53} are added. Incubate the sample during 2 hours a 60° C. under stirring. Add 1.43 g of sodium cyanoborohydride (NaBH$_3$CN). Incubate the sample at 60° C. under stirring overnight. Centrifugate and eliminate the supernatant. Wash at least once with 30 and 50 ml of distilled water. Centrifugate again and eliminate the supernatant. Add 50 ml of the solvent mixture chloroform:methanol:NH$_4$OH 15M (60:35:8; V/V/V). Incubate the sample during 1 hour at room temperature under stirring. Centrifugate, dry the supernatant into a rotating desiccator. Place the dried sample in a minimum volume of water. Lyophilize and store the sample in freezer at −20° C.

Example 16

Evaluation of the Activity Against HCV

The evaluation of antiviral activity of the compounds THE 08/01, THE 10/01 and THE 10/09 (see Table 1) have been assessed on JFH-1 HCV according to the techniques known in the art. The abstracted summary is hereby enclosed.

Materials and Methods

1. Phase I: Production of the Recombinant Virus

Recombinant virus was produced by transfection of recombinant RNA into the cell line of human hepatoma Huh7.5. The obtained virus was cultured on the same cellular line, and then the focus-forming units (FFU) were counted before using in the subsequent phases. For this purpose cells have been seeded in microplates at a concentration of 10.000 cells per each well. After 18 hours cells were infected with serial dilutions of viral suspension and incubated for 6 hours, followed by replacement of the medium with fresh medium. After 3 days the cell layer was fixed and coloured with the anti-HCV-core antibodies, and the focus-forming units in each dilution were counted.

2. Phase II: Evaluation of the Activity for an in Vitro Infection (Short Term)

A monolayer of Huh7.5 cells seeded on plates of 24 well plates has been infected with JFH-1 at a moltiplicity of infection (MOI) equal to 0.01. After incubation for 1.5 hour at 37° C., which allows the viral adsorption, the cellular monolayer was washed trice with medium. Thereafter, culture medium MEM (Minimal Essential Medium) containing serial dilutions of the compounds under testing (from 0.004 µg/ml to 0.5 µg/ml) was then added. The test has been carried out in triplicate, while simultaneously a blank control has been also prepared. The cells have been incubated at 37° C., in 5%, $CO_2$ for 2 days. Finally, the inhibitory effect on the viral replication has been measured by means of the FFU technique.

3. Results and Conclusions

The tested compounds showed a weak inhibition on JFH-1 HCV. More particularly, results it were remarkable for THE 10/09.

The abstracted results are summarized in FIG. 5.

REFERENCES

1. Das P. et al. "*Free energy simulations reveal a double mutant avian H5N1 virus hemagglutinin with altered ceptor binding specificity.*", J. Comput. Chem. 2009, 30 (11): p. 1654-63.
2. Iwata T. el al. "*Theoretical analysis of binding specificity of influenza viral hemagglutinin to avian and human receptors based on the fragment molecular orbital method.*", Comput. Biol. Chem. 2008, 32 (3):p. 198-211.
3. Xu D. el al. "*Distinct glycan topology for avian and human sialopentasaccharide receptor analogues upon binding different hemoagglutinings: a molecular dynamics perspective.*", J. Mol. Biol. Epub. 2009 Feb. 5, 2009, 387 (2): p. 465-91.
4. Wilson I. A. et al. "*Structure of the heamoagglutinin membrane glycoprotein of influenza virus at 3 Å resolution*", Nature 1981, 289: p. 366-73.
5. Schriver Z. et al. "*Context-specific target definition in influenza a virus hemagglutinin-glycan receptor interactions*", Chem. Biol. 2009 Aug. 28, 16 (8): p. 803-814.
6. Wang C. C. et al. "*Glycans on influenza hemagglutinin effect receptor binding and immune response.*", Proc. Natl. Acad. Sci. U.S.A., 2009, Oct. 12.
7. Varghese J. N. et al. "*Structure of the influenza virus glycoprotein antigen neuraminidase at 2.9 Å resolution*", Nature 1983, 303: p. 35-40.
8. Colman P. M. et al. "*Structure of the catalytic and antigenic sites in influenza virus neuraminidase*", Nature 1983, 303: p. 41-44.
9. Taylor N. R., von Itzstein M. "*Molecular modeling studies on ligand binding to sialidase from influenza virus and the mechanisms of catalysis.*", J. Med. Chem. 1994, 37 (5): p. 616-24.
10. D'Ursi P. et al "*Virtual screening pipeline and ligand modelling for H5N1 neuraminidase*", Biochem. Biophys. Res. Comm. 209 June 12, 383 (4): p. 445-9.
11. Herrier Georg, et al., "*A synthetic sialic acid analogue is recognized by influenza C virus as a receptor but is resistant to the receptor-destroying enzyme*", J. Biol. Chem. 1992, 2567 (8): p. 12501-12505.
12. Herrier G. et al. "*9-O-acetylated sialic acid, a receptor determinant for influenza C virus and coronavirus*" Behring Inst. Mitt. 1991, 89: p. 177-84.
13. Schwegmann-Wessels C. et al. "*Sialic acids as receptors determinants for coronavirus*" Glycoconj. J. 2006, 23 (1-2): p. 51-8.

14. Yamashita M. et al., "*CS-8958, a prodrug of the new neuraminidase Inhibitor R-125489, shows long-acting anti-influenza virus activity*", Antimicrob. Agents Chemother. 2009, 53(1): p. 186-92.
15. Moscona A. "*Medical management of influenza infection*", Annu. Rev. Med. 2008, 59: p. 397-413.
16. Centers for Disease Control and Prevention (CDC) "*High levels of adamantine resistance among influenza A (H3N2) viruses and interim guidelines for use of antiviral agents-United States, 2005-06 influenza season*.", MMWR Morb. Mortal Wkly Rep. 2006, 55 (2): p. 44-6.
17. Stephenson I., et al. "*Antiviral treatment and prevention of seasonal influenza: a comparative review of recommendations in the European Union*", J. Clin. Virol. 2008, 42 (3): p. 244-8.
18. Centers for Disease Control and Prevention (CDC) "*Oseltamivir-resistant 2009 pandemic influenza A (H1N1) virus infection in two summer campers receiving prophylaxis-North Carolina, 2009*", MMWR morb. Mortal Wkly Rep. 2009 Sep. 11, 58 (35): p. 969-72.
19. Collins P. J. et al. "*Structural basis for oseltamivir resistance of influenza viruses*", Vaccine 2009 Oct. 23, 27 (45): p. 6317-23.
20. Carr M. J. et. al. "*Rapid molecular detection of the H275Y oseltamivir resistance gene mutation in circulating influenza A (H1N1) viruses*." J. Virol. Methods 2008, 153 (2): p. 257-262.
21. Stephenson I. et al. "*Neuraminidase Inhibitor Resistance after Oseltamivir Treatment of Acute Influenza A and B in Children*" Clin. Infect. Dis. 2009, Gen. 9, in stampa;
22. Guo L. et al. "*Rapid identification of oseltamivir-resistant influenza A(H1N1) viruses with H274Y mutation by RT-PCR/restriction fragment length polymorphism assay.*" Antiviral Res. Epub 2009 Gen. 31, 2009 April, 82 (1): p. 29-33.
23. Gooskens J. et al. "*Morbidity and mortality associated with nosocomial transmission of oseltamivir-resistant influenza A(H1N1) virus.*" JAMA Epub 2009 Mar. 2, 2009 Mar. 11, 301 (10): p. 1042-6.
24. Bolotin S. et al. "*Development of a novel real-time reverse-transcriptase PCR method for the detection of H275Y positive influenza A H1N1 isolates.*"3 Virol Methods. Epub 2009 Gen. 30, 2009 Giu., 158 (1-2): p. 190-194.
25. Dharan N. J. et al. Oseltamivir-Resistance Working Group "*Infections with oseltamivir-resistant influenza A(H1N1) virus in the United States.*" JAMA Epub 2009 Mar. 2, 2009 Mar. 11, 301 (10), p. 1034-41.
26. Doms R. W. et al. "*Variant influenza virus hemagglutinin that induces fusion at elevated pH*", J. Virol. 1986, 57 (2): p. 603-613.
27. Takahashi T. el al. "*Duck and animal pandemia influenza A viruses retain sialidase activity under low pH conditions*" J. Biochem. 2001, 130: p. 279-283.
28. Itzstein L. M. von el al. "*Rational design of potent sialidase-based inhibitors of influenza virus replication*", Nature 1993, 363 (6428): p. 418-423.
29. Babu Y. S. et al.: "*Discovery of a novel, highly potent, orally active, and selective influenza neuraminidase inhibitor through structure-based drug design.*", J. Med. Chem. 2000, 43 (19): 3482-86.
30. Martindale 33.ma Ed. (2002) p. 639-43.
31. Chen Y. et al. "*Dengue virus infectivity depends on envelope protein binding to target cell heparan sulfate.*", Nat. Med. 1997, 3: p. 866-71.
32. Kimura T. et al. "*Analysis of virus-cell binding characteristics on the determination of Japanese encephalitis virus susceptibility.*", Arch, Virol. 1994, 139: p. 239-251.
33. Kopecky J. et al. "*A putative host cell receptor for tick-borne encephalitis virus identified by anti-idiotypic antibodies and virus affinoblotting.*", Intervirology 1999, 42: 9-16.
34. Maldov D. G. et al. "*Tick-borne encephalitis virus interaction with the target cells.*" Arch. Virol. 1992, 127: p. 321-325.
35. Ramos-Castaneda J. et al. "*A 65-kDa trypsin-sensible membrane cell protein as a possible receptor for dengue virus in cultured neuroblastoma cells.*" J. Neurovirol. 1997, 3: p. 435-440.
36. Salas-Benito J. S. et al. "*Identification of two surface proteins from C6/36 cells that bind dengue type 4 virus.*" J. Virol. 1997, 71: p. 7246-7252.
37. Bernfield M-et al. "*Functions of cell surface heparan sulfate proteoglycans.*" Annu. Rev. Biochem. 1999, 68: p. 729-777.
38 Chambers T. J. et al. "*Flavivirus genome organization, expression, and replication.*", Annu. Rev. Microbiol. 1990, 4: p. 649-688.
39. Monath T. P. et al. "*Flaviviruses.*", in Fields B. N., Knipe D. M., Howley P. M., Editors. Fields Virology, 3rd ed., Vol. 1, 1996, Philadelphia, Pa., Lippincott-Raven Publishers, p. 961-1034.
40. Rey F. A. et al., "*The envelope glycoprotein from tick-borne encephalitis virus at 2 angstrom resolution.*", Nature 1995, 375: p. 291-298.
41. Lobigs M. et al. "*Host cell selection of Murray Valley encephalitis virus variants altered at an RGD sequence in the envelope protein and in mouse virulence.*", Virology 1990, 176: p. 587-595.
42. Ruoslahti E. et al. "*New perspectives in cell adhesion: RGD and integrins.*", Science 1987, 238: p. 491-497.
43. McAda P. C. et al. "*Partial nucleotide sequence of the Japanese encephalitis virus genome.*", Virology 1987, 158: p. 348-360.
44. Rice C. M. et. al. "*Nucleotide sequence of yellow fever virus: implications for flavivirus gene expression and evolution.*" Science 1985, 229: p. 726-733
45. Castle E. et al. "*Sequence analysis of the viral core protein and the membrane-associated proteins V1 and NV2 of the flavivirus West Nile virus and of the genome sequence for these proteins.*", Virology 1985, 145: p. 227-236.
46. Coia G. et al. "*Nucleotide and complete amino acid sequences of Kunjin virus: definitive gene order and characteristics of the virus-specified proteins.*" J. Gen. Virol. 1988, 699: p. 1-21.
47. Trent D. W. et. al. "*Partial nucleotide sequence of St. Louis encephalitis virus RNA: structural proteins, NS1, ns2a, and ns2b.*", Virology 1987, 156: p. 293-304.
48. Hahn Y. S. et al "*Nucleotide sequence of dengue 2 RNA and comparison of the encoded proteins with those of other flaviviruses.*", Virology 1988, 162: p. 167-180.
49. Mackow E. et al. "*The nucleotide sequence of dengue type 4 virus: analysis of genes coding for nonstructural proteins.*", Virology 1987, 159: p. 217-228.
50. Mason P. W. et al. "*Sequence of the dengue-1 virus genome in the region encoding the three structural proteins and the major nonstructural protein NS1.*", Virology 1987, 161: p. 262-267.
51. Mandl C. W. et al. "*Sequence of the structural proteins of tick-borne encephalitis virus (western subtype) and comparative analysis with other flaviviruses.*", Virology 1988, 166: p. 197-205.

52. Hahn C. S. et al. "*Comparison of the virulent Asibi strain of yellow fever virus with the 17D vaccine strain derived from it.*", Proc. Natl. Acad. Sci. USA. 1984, 84: p. 2019-2023.
53. Jackson T. et al. "*Arginine-glycine-aspartic acid-specific binding by foot-and-mouth disease viruses to the purified integrin alpha(v)beta3 in vitro.*", J. Virol. 1997, 71: p. 8357-8361.
54. Neff S. et al. "*Foot-and-mouth disease virus virulent for cattle utilizes the integrin alpha(v)beta3 as its receptor.*" J. Virol., 72: p. 3587-3594.
55. Roivainen M. et al. "*Entry of coxsackievirus A9 into host cells: specific interactions with alpha v beta 3 integrin, the vitronectin receptor.*" Virology 1994, 203: p. 357-365.
56. Tyler K. L. et al "*Pathogenesis of viral infection.*" Fields Virology. 3rd ed., Fields B. N., Knipe D. M, Howley P. M. Editors. Philadelphia 1996, Pa. Lippincott-Raven, p. 173-218.
57. Kimura, T. et al. "*Analysis of virus-cell binding characteristics on the determination of Japanese encephalitis virus susceptibility.*" Arch. Virol. 1994, 139, p. 239-251.
58. Maldov D. G. et al. "*Tick-borne encephalitis virus interaction with the target cells.*" Arch. Virol. 1992, 127: p. 321-325.
59. Salas-Benito J. S.; del Angel R. M. "*Identification of two surface proteins from C6/36 cells that bind dengue type 4 virus.*" J. Virol. 1997, 71: p. 7246-7252.

The invention claimed is:

1. A compound of structural formula (I):

(I)

wherein:

X is —O—;

R is —H;

$R^1$ is —(NH)-(T) or —NH—C(NH)—NH-(T), wherein- (T) is selected from

-(T-1)

wherein —$R^5$ is —H, —$CH_3$, —$C_2H_5$; —$R^6$ is —NH—CO—$CH_3$, —NH—CO—$C_2H_5$; and —$R^7$ is —O—CH—$(C_2H_5)_2$ or

-(T-2)

or

-(T-3)

or

-(T-4)

wherein —Z is —H, —CH—$(C_2H_5)_2$, —CO—$(CH_2)_6$—$CH_3$;

$R^2$ is —OH;

$R^3$ is —NH—CO—CH3;

$R^4$ is, independently from R1, —CHOH—CHOH—CH2-OH, —(W), —CHOH—CH2-(W), or —CH2-(W); and —(W) is either:

-(W-1)

wherein:

$R^8$ is —NH—, —$CH_2$—NH—, —$CH(CH_3)$—NH—, $C(CH_3)_2$—$CH_2$—NH—;

$R^9$ is —H, —$CH_3$;

$R^{10}$ is —H, —CH$_3$

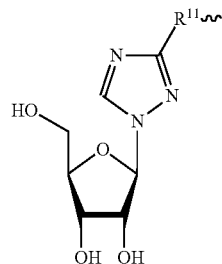

-(W-2)

or wherein —R$^{11}$ is —NH—, —CO—NH— or —C(NH)—NH— and linear or branched C$_{1-4}$ carboxy mono or poly esters, addition salts, solvates, resolved enantiomers and purified diastereoisomers thereof.

2. A compound selected from the group consisting of the following structural formulae:

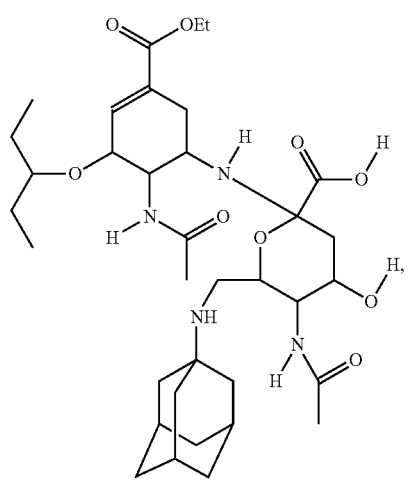

Compound THE08/01 (Example 7)

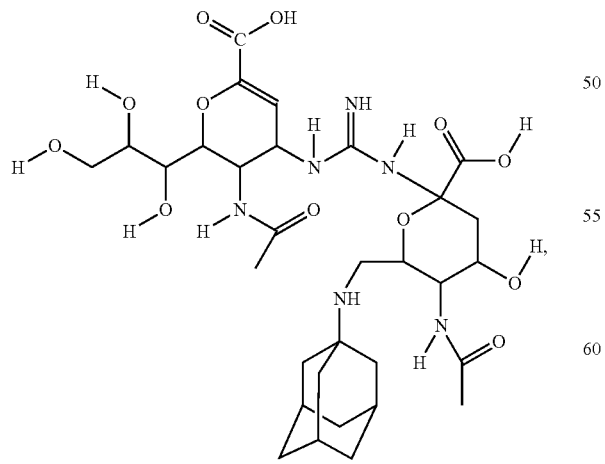

Compound THE10/01 (Example 8)

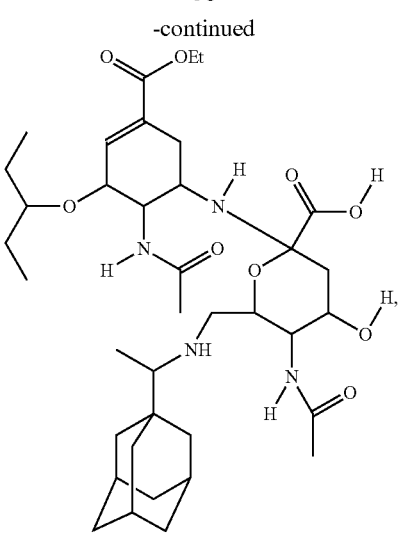

Compound THE10/04 (Example 12)

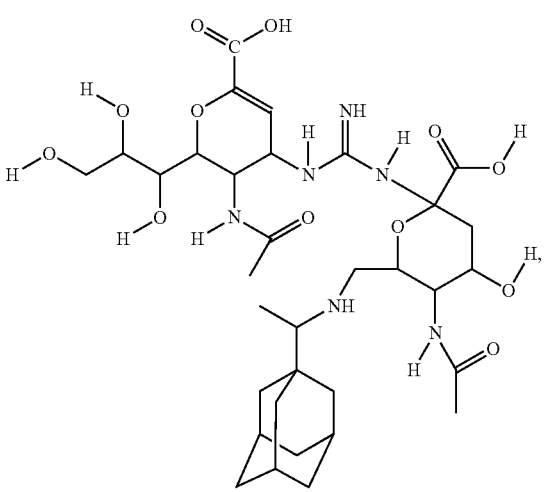

Compound THE10/05 (Example 13)

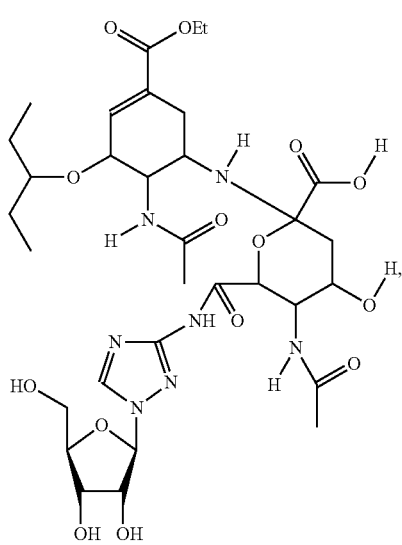

Compound THE10/09 (General)

-continued

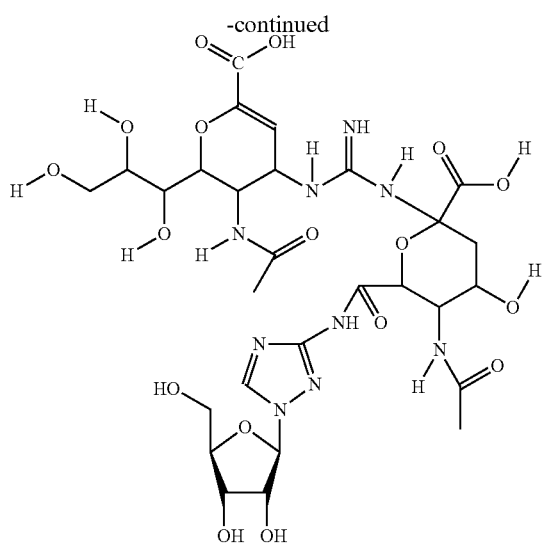

Compound THE10/10 (General)

and linear or branched C1-4 carboxy mono or poly esters, addition salts, solvates, resolved enantiomers and purified diastereoisomers thereof.

3. A pharmaceutical composition comprising only a compound of claim 1 in a pharmaceutically acceptable carrier.

4. A method for treating at least one of a viral, bacterial or protozoarian infection in a patient in need thereof, comprising administering to the patient a therapeutically effective amount of a compound according to claim 1.

5. The method of claim 4 wherein the infection is caused by hemagglutinin (HA), neuraminidase (NA), the protein $M_2$ and/or RNA polymerase containing virus, bacteria, or protozoa.

6. The method of claim 4 wherein the infection is caused by hemagglutinin (HA), neuraminidase (NA), the protein $M_2$ represented by influenza virus type A and B or by mutations therefrom.

7. The method of claim 4, wherein said infection comprises al least one of RNAm-guanylyltranspherase o RNA polymerase represented by hepatitis virus type C (HCV) or by mutations therefrom.

8. The method of claim 4, further comprising: co-administering a therapeutically effective quantity of a compound active against the flu virus type A and B or their resistant mutations therefrom.

9. The method of claim 4, further comprising: co-administering a therapeutically effective quantity of a compound active against hepatitis virus type C (HCV) or their mutations therefrom.

10. The method of claim 9, wherein said co-administered compound active against HCV is alpha-interferon.

* * * * *